(12) United States Patent
Gamada

(10) Patent No.: US 7,435,234 B2
(45) Date of Patent: Oct. 14, 2008

(54) NON-SURGICAL CORRECTING ABNORMAL KNEE LOADING

(75) Inventor: Kazuyoshi Gamada, Hiroshima (JP)

(73) Assignee: The Regents of the University of Colorado, a Body Corporate, Denver, CO (US)

( * ) Notice: Subject to any disclaimer, the term of this patent is extended or adjusted under 35 U.S.C. 154(b) by 0 days.

(21) Appl. No.: 10/596,341

(22) PCT Filed: Dec. 10, 2004

(86) PCT No.: PCT/US2004/041304

§ 371 (c)(1),
(2), (4) Date: Jun. 9, 2006

(87) PCT Pub. No.: WO2005/058193

PCT Pub. Date: Jun. 30, 2005

(65) Prior Publication Data

US 2007/0100265 A1     May 3, 2007

Related U.S. Application Data

(60) Provisional application No. 60/543,515, filed on Feb. 10, 2004, provisional application No. 60/529,139, filed on Dec. 12, 2003.

(51) Int. Cl.
    *A61F 5/00* (2006.01)
(52) U.S. Cl. .......................................... 602/26; 602/16

(58) Field of Classification Search ..................... 602/5, 602/16, 26, 27–29, 23
See application file for complete search history.

(56) References Cited

U.S. PATENT DOCUMENTS

| 4,493,316 A | 1/1985 | Reed et al. |
| 4,503,846 A | 3/1985 | Martin |
| 4,520,802 A | 6/1985 | Mercer et al. |
| 4,542,900 A | 9/1985 | Ray |
| 4,554,913 A | 11/1985 | Womack et al. |

(Continued)

FOREIGN PATENT DOCUMENTS

| WO | WO 91/18565 | 12/1991 |
| WO | WO 98/38964 | 9/1998 |

OTHER PUBLICATIONS

Townsend Design, "Osteoarthritis Bracing Solutions," http://www.townsenddesign.com/perspectives ,Downloaded Oct. 4, 2004.

*Primary Examiner*—Kim M Lewis
(74) *Attorney, Agent, or Firm*—Greenlee, Winner and Sullivan, P.C.

(57) ABSTRACT

The invention provides hinges for use in knee braces to correct and prevent knee pathology. Further provided are knee braces comprising the hinges of the present invention to correct and prevent knee pathology including osteoarthritis. Also provided are methods of treating knee pathology by using the hinges and braces of the present invention to apply a corrective rotational force and an off-loading force to the affected knee compartment.

18 Claims, 12 Drawing Sheets

U.S. PATENT DOCUMENTS

| | | |
|---|---|---|
| 4,637,382 A | 1/1987 | Walker |
| 4,723,539 A | 2/1988 | Townsend |
| 4,726,362 A | 2/1988 | Nelson |
| 4,751,920 A | 6/1988 | Mauldin et al. |
| 4,796,610 A | 1/1989 | Cromartie |
| 4,856,501 A | 8/1989 | Castillo et al. |
| 4,886,054 A | 12/1989 | Castillo et al. |
| 4,890,607 A | 1/1990 | Townsend |
| 4,940,044 A | 7/1990 | Castillo |
| 5,107,824 A * | 4/1992 | Rogers et al. .............. 602/16 |
| 5,135,469 A | 8/1992 | Castillo |
| 5,230,697 A | 7/1993 | Castillo et al. |
| 5,259,832 A | 11/1993 | Townsend et al. |
| 5,277,698 A | 1/1994 | Taylor |
| 5,288,287 A | 2/1994 | Castillo et al. |
| 5,292,303 A | 3/1994 | Bastyr et al. |
| 5,303,716 A | 4/1994 | Mason et al. |
| 5,316,547 A | 5/1994 | Gildersleeve |
| 5,330,418 A | 7/1994 | Townsend et al. |
| 5,383,845 A | 1/1995 | Nebolon |
| 5,409,449 A | 4/1995 | Nebolon |
| 5,456,659 A | 10/1995 | Gildersleeve et al. |
| 5,458,565 A | 10/1995 | Tillinghast, III et al. |
| 5,509,894 A | 4/1996 | Mason et al. |
| 5,527,268 A | 6/1996 | Gildersleeve et al. |
| 5,611,774 A | 3/1997 | Postelmans |
| 5,672,152 A | 9/1997 | Mason et al. |
| 5,693,007 A | 12/1997 | Townsend |
| 5,743,865 A | 4/1998 | Townsend |
| 5,766,140 A | 6/1998 | Tillinghast, III et al. |
| 5,772,618 A | 6/1998 | Mason et al. |
| 5,792,086 A | 8/1998 | Bleau et al. |
| 5,797,864 A | 8/1998 | Taylor |
| 5,807,294 A | 9/1998 | Cawley et al. |
| 5,827,208 A | 10/1998 | Mason et al. |
| 6,413,232 B1 | 7/2002 | Townsend et al. |
| 6,500,139 B1 | 12/2002 | Townsend et al. |
| 6,540,708 B1 | 4/2003 | Mansoeizer |
| 6,540,709 B1 | 4/2003 | Smits |
| 6,551,264 B1 | 4/2003 | Cawley et al. |
| 6,635,024 B2 | 10/2003 | Hatton et al. |
| 6,719,713 B2 | 4/2004 | Mason |
| 6,875,187 B2 | 4/2005 | Castillo |
| 6,936,019 B2 | 8/2005 | Mason |
| 6,981,957 B2 | 1/2006 | Knecht et al. |
| 7,044,925 B2 | 5/2006 | Castillo et al. |
| 7,059,329 B2 | 6/2006 | Mason et al. |
| 7,060,045 B2 | 6/2006 | Mason et al. |
| 2003/0149386 A1 | 8/2003 | Ceriani et al. |
| 2004/0002674 A1 | 1/2004 | Sterling |
| 2004/0054311 A1 | 3/2004 | Sterling |
| 2005/0159691 A1* | 7/2005 | Turrini et al. .............. 602/16 |

* cited by examiner

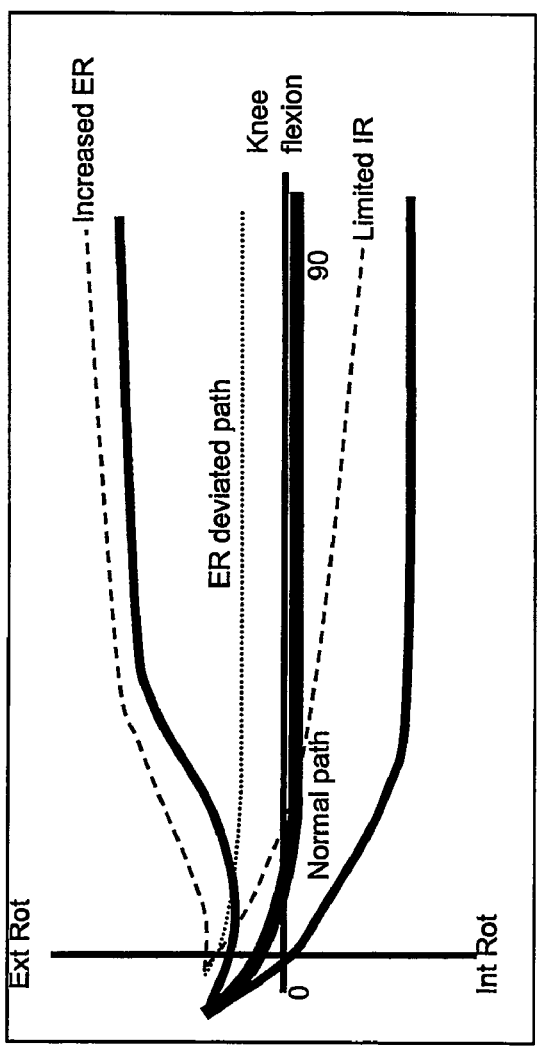
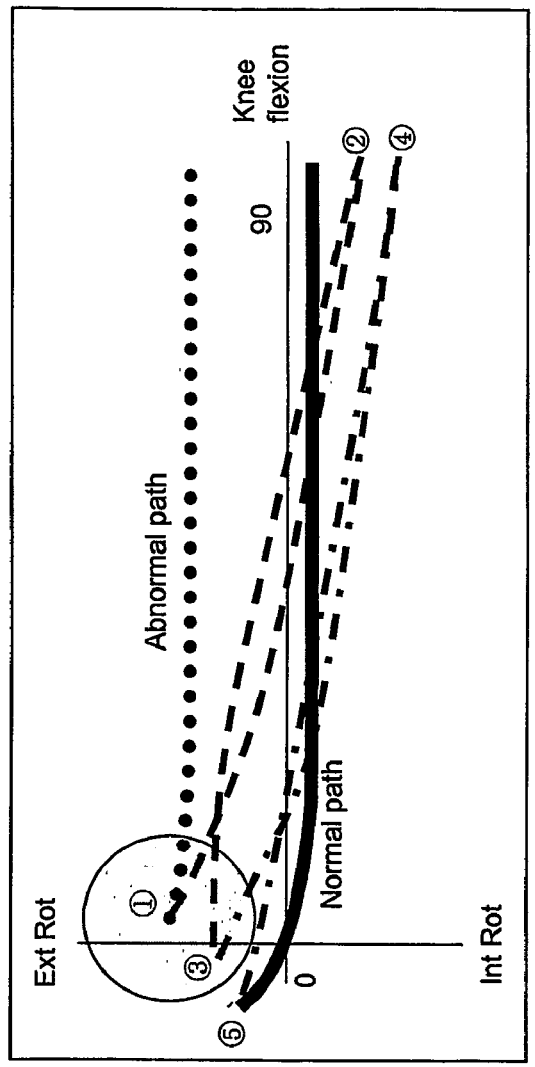
FIG 1A
FIG 1B

● Cylindrical axis
○ Center of Rotation

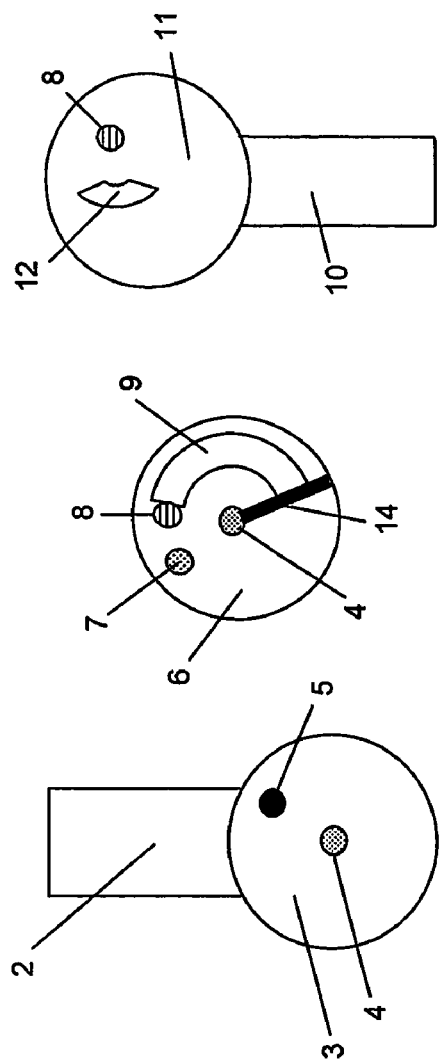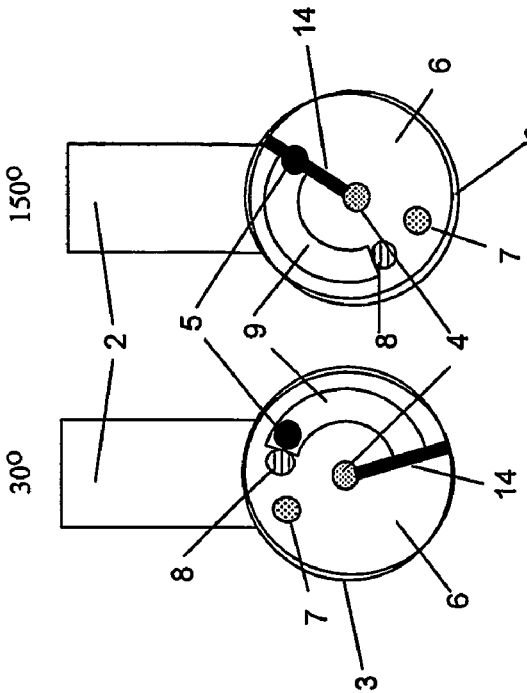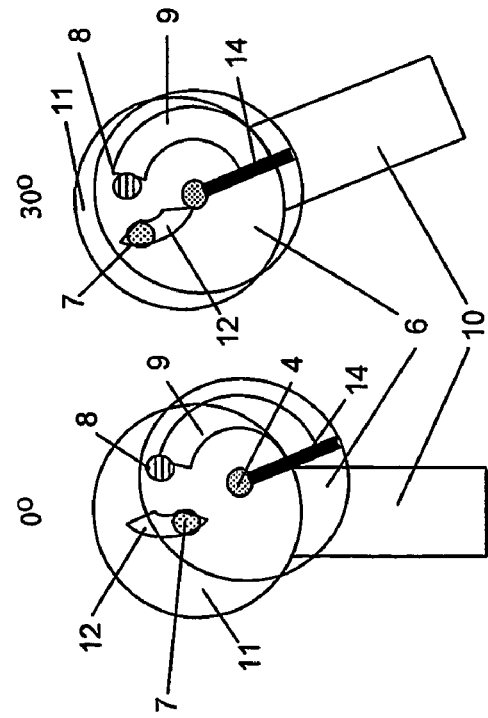

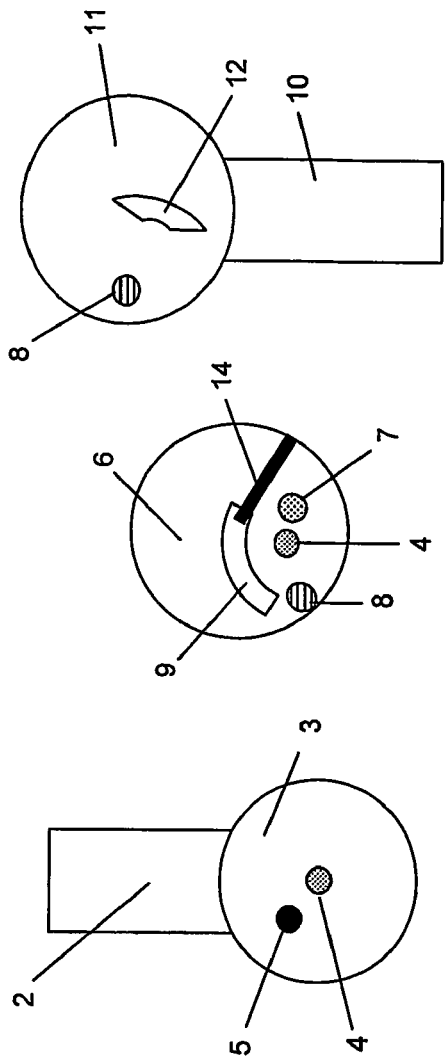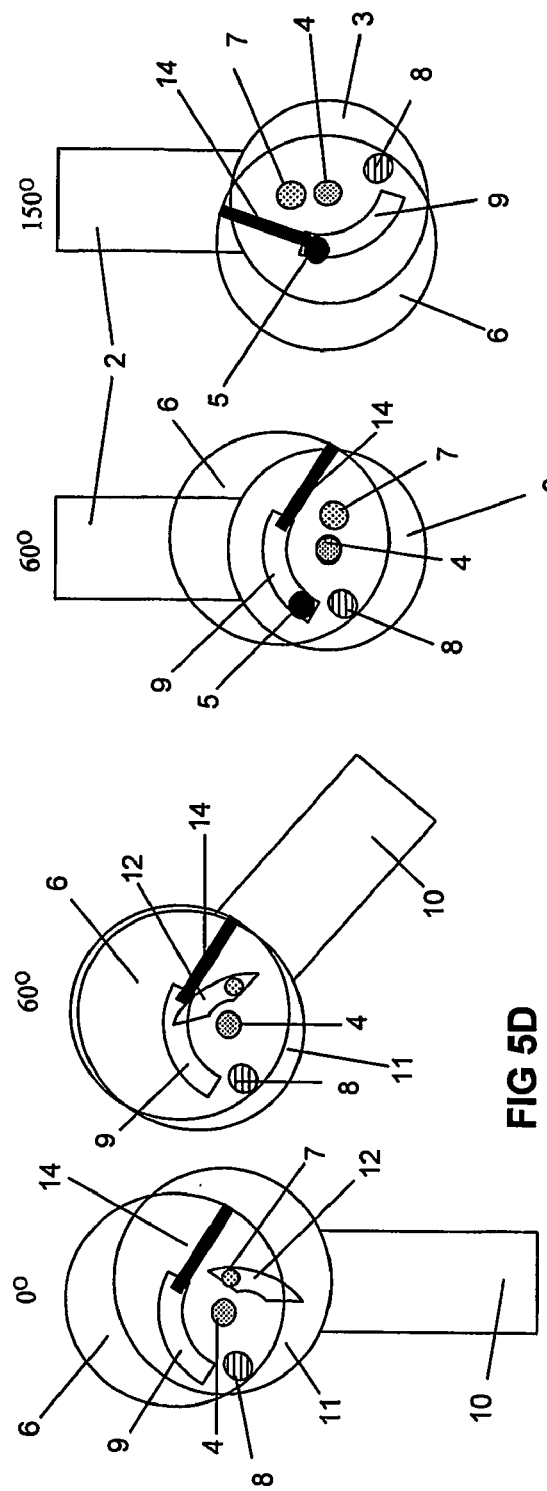

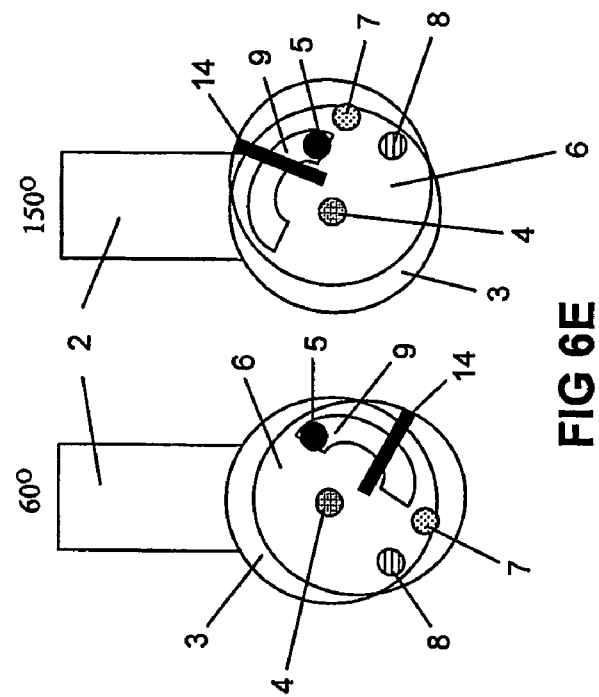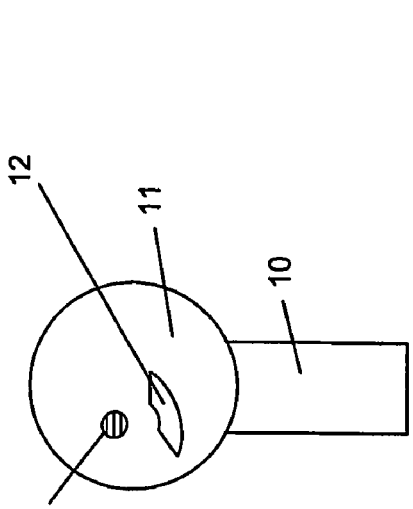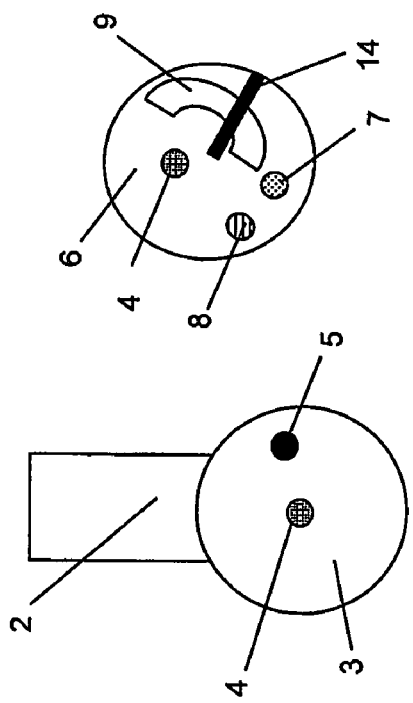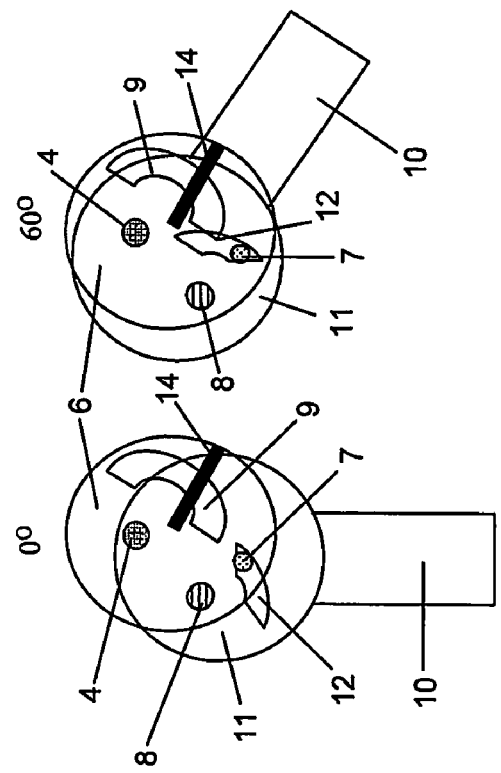
FIG 6A  FIG 6B  FIG 6C  FIG 6D  FIG 6E

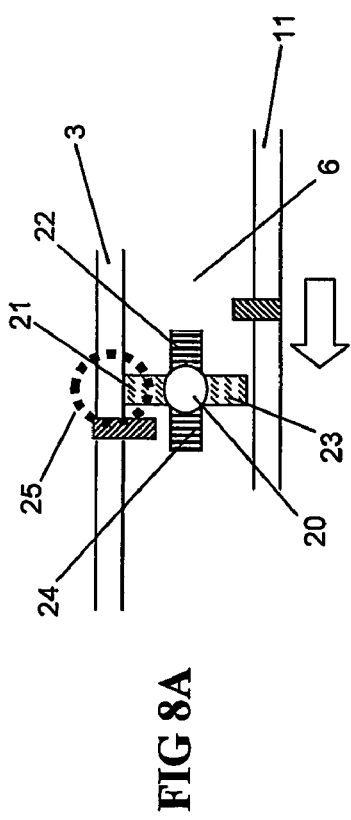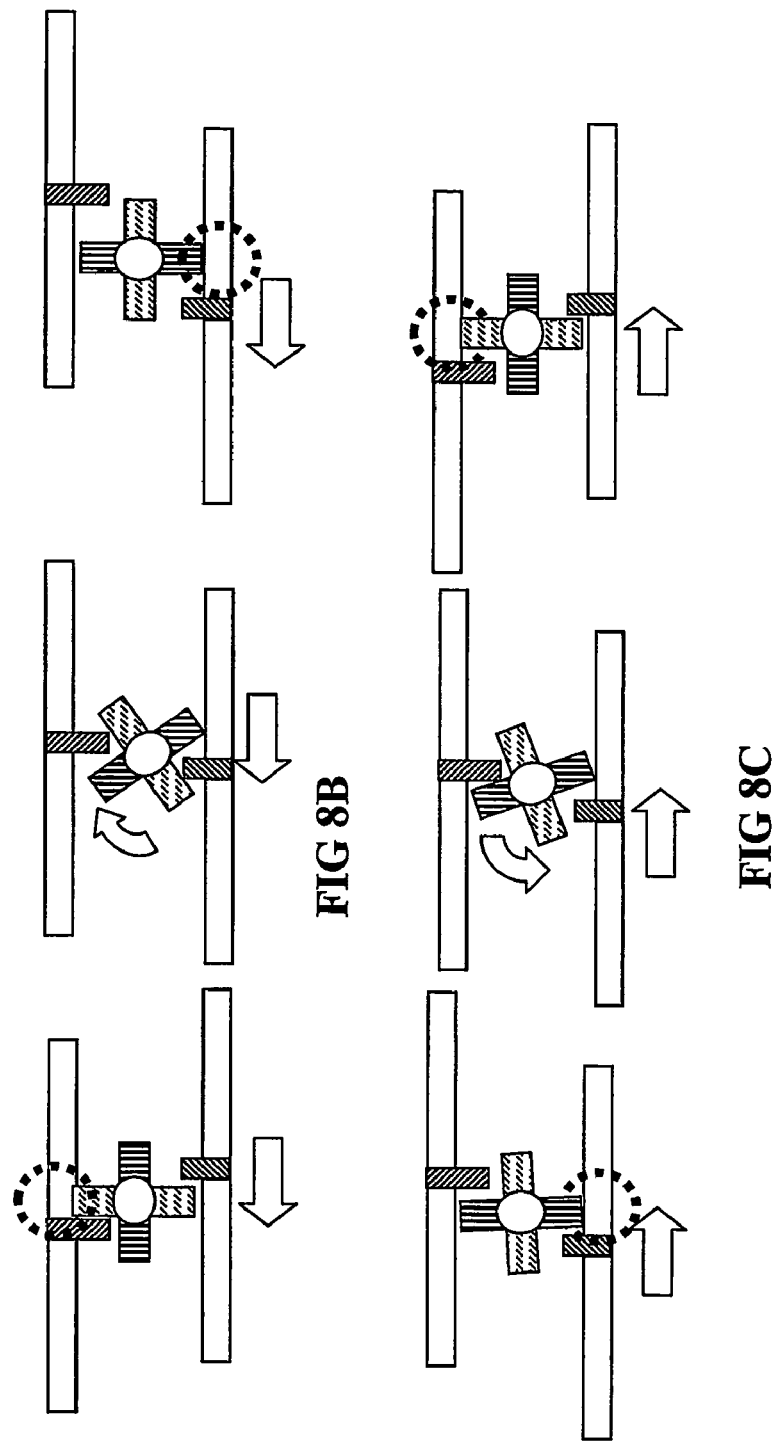
FIG 8A
FIG 8B
FIG 8C

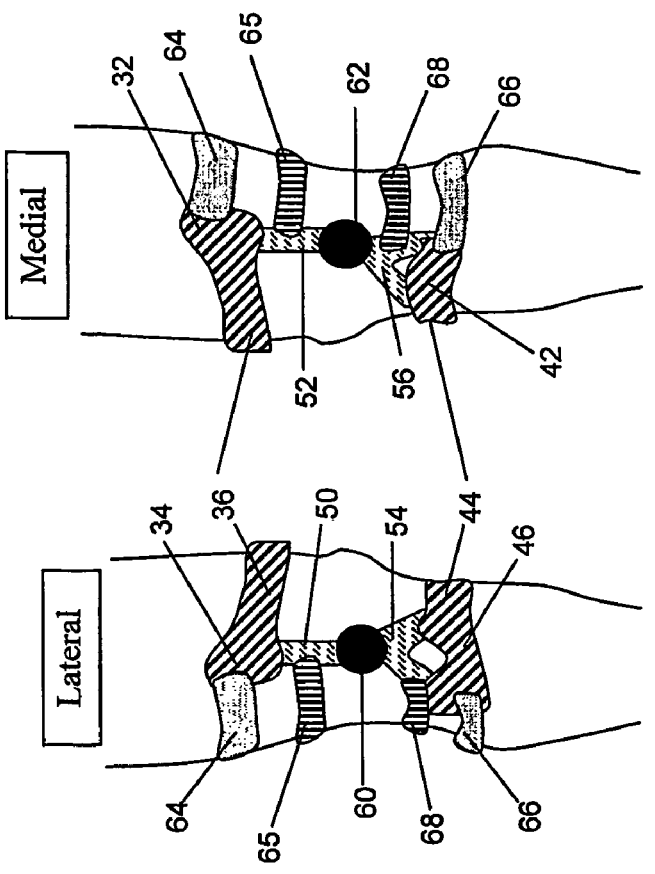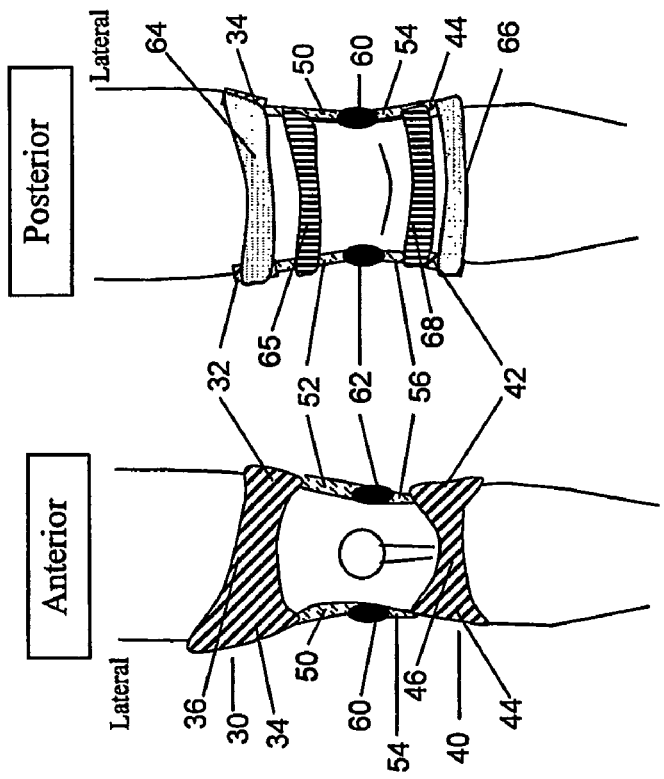

NON-SURGICAL CORRECTING ABNORMAL KNEE LOADING

CROSS-REFERENCE TO RELATED APPLICATIONS

This application is a national stage application under 35 U.S.C. §371 of PCT/US04/41304, filed Dec. 10, 2004, which takes priority from U.S. Provisional patent application nos. 60/529,139 filed Dec. 12, 2003 and 60/543,515 filed Feb. 10, 2004, all of which are incorporated by reference in their entirety herein.

FIELD OF INVENTION

The invention relates to correction and prevention of osteoarthritis in knees and more specifically knee braces, hinges used in knee braces and methods to prevent osteoarthritis and correct abnormal knee alignment.

BACKGROUND OF THE INVENTION

The knee is composed of three bones, the patella (knee cap), the femur and the tibia. The meniscus (cartilage), composed of the lateral and medial menisci, cushion and distribute the weight of the femur uniformly across the joint. The gaps between the tibia and femur on the inside and outside of the knee are called the "medial" and "lateral" compartments, respectively. The condyle is the smooth, rounded end of the femur that allows the femur to move easily over the surface of the meniscus on the tibia. The medial and lateral femoral condyles are generally spherical with different radii, are asymmetric with respect to one another, and articulate upon the tibial plateaus. The ligaments and tendons control the motion of the knee joint. The tendons connect the patella; the ACL (anterior cruciate ligament) and PCL (posterior cruciate ligament) prevent the tibia from sliding forward or backward and limit the tibial rotation; the collateral ligaments minimize side-to-side motion and stabilize the knee.

The complicated connections of the knee joint permit the joint to have multiple degrees of freedom. The joint has three axes of rotation: flexion and extension, abduction and adduction, and internal/external rotation between the femur and the tibia. A straight leg is said to be at full extension, and during normal human gait motion the bent knee position averages about 60 degrees of flexion. The range of motion can increase with physical activity (e.g. cycling, running). As the leg undergoes flexion or extension, there is a complex asymmetric motion of the knee joint. Adduction (varus) motion occurs as the ankle moves toward the body's midline with flexion. With extension, the ankle moves away from the body's midline, resulting in abduction (valgus). In addition, the tibia internally rotates with respect to the femur as the knee flexes. As the knee extends, the tibia rotates externally. The tibia also has proximal/distal and medial/lateral motion, with respect to the femur, during flexion/extension. See U.S. Pat. Pub. Nos. 2004/0054311 and 2004/0002674, hereby incorporated by reference, for a description of knee motion as a function of extension/flexion.

Because the knee joint is used so often, and is one of the most mobile and flexible joints in the body, it is vulnerable to injury. The knee is kept in alignment by the tendons and ligaments. Malalignment of the knee joint can occur when any of the tendons or ligaments is damaged. In particular, malalignment occurs when the tibia is translated and rotated relative to the femur. Malalignment of the tibia causes abnormal loading of forces across the knee, disrupts the normal knee joint motion, and osteoarthritis (OA) of the knee. Knee OA is one of the most common orthopaedic problems with about six percent of U.S. adults over 30 years of age suffering from this disease. The total cost of knee OA was estimated as $15.5 billion in 1994. Advanced OA often requires surgery to restore leg alignment, physical function, and reduce knee joint pain.

Treatment for knee injury, particularly knee OA, often involves the combined use of knee braces and physical therapy on the knee joint, including muscle exercise. However, many prior art knee braces apply a unilateral varus force on the valgus knee or valgus force on the varus knee to relieve pressure on the side of the knee that is injured when the leg is fully extended (see U.S. Pat. No. 5,277,698). These prior art braces, called "off-loading" braces, can increase the joint space on the compressed side of the knee, thereby reducing the unbalanced force across the knee joint, when the leg is fully extended. For example, UNLOADER® (Generation II) brand knee braces reduce the load on the affected compartment by a three-point force system and a single hinge. To generate sufficient force to correct the compressive stress, off-loading braces require relatively long lever arms and strong frames. These off-loading braces, therefore, are relatively bulky, heavy, and tend to slide down the leg. These braces do not, however, compensate for the rotational malalignment of the tibia. Instead, they apply the major force only when the leg is fully extended. When the leg is fully extended, however, accessory movement of the knee is restricted (the tibia cannot rotate). Thus, any force applied to the fully extended leg is not effective in correcting the underlying rotational malalignment of the tibia.

Most braces do not properly simulate the complex three-dimensional motion of the knee joint. For example, many braces are designed to protect from external impact to the knee. Other braces only permit limited motion of the knee joint without providing for the more complicated multi-dimensional motion of the joint. U.S. Pat. No. 4,723,539 provides a knee brace hinge with a slot and slot follower permitting only an anterior/posterior motion during flexion. The center of rotation, however, remains fixed. Another type of brace hinge has linking and pivot members wherein the pivot point changes during rotational movement (U.S. Pat. No. 5,230,697), but does not control other motions. Still other braces that attempt to control knee motion in three-dimensions are bulky. See, e.g. U.S. Pat. Nos. 5,792,086 and 5,107,824. There is a need in the art to correct the rotational malalignment, as well as lateral or medial translation, of the tibia during the leg's swing phase so as to correct abnormal loading force of the knee joint as the leg nears full extension. The knee braces of the present invention do not require a non-physiological force to be applied to the knee joint, but instead restore normal knee motion by applying appropriate physiological forces during flexion and extension. Therefore, the present invention's knee braces can be relatively small and lightweight, thereby increasing the user's comfort, while restoring the normal envelope of knee motion.

BRIEF SUMMARY OF THE INVENTION

The present invention reduces the effects of OA and abnormal loading of the knee by applying a force to correct tibial translational and rotational malalignment. Accordingly, the present invention provides a method of reducing abnormal rotational alignment by applying a torsional force to correct abnormal rotational alignment during flexion.

In one embodiment, the invention comprises hinges suitable for use in orthopedic knee braces. The hinge can comprise three shells: an inner shell, a middle shell and an outer shell. The middle shell can be rotatably engaged to the inner shell and the outer shell can be rotatably engaged to the middle shell. Rotatably engaged shells have a co-axis about which the shell rotates. The middle shell can rotate relative to the inner shell about an inner-middle shell co-axis. The outer shell can rotate relative to the middle shell about a middle-outer shell co-axis. Depending on the knee condition to be corrected, the co-axis can be located anywhere on the relevant shell. Generally, the inner-middle shell co-axis is centered on the center of the inner shell and the middle-outer shell co-axis is located off-center of the middle shell.

The inner and middle shells each further comprise an inner and middle shell protuberance, respectively. The middle and outer shells each further comprise a middle and outer shell slot, respectively. The inner shell protuberance tracks the middle shell slot, thereby constraining the rotation of the middle shell relative to the inner shell. The middle shell protuberance tracks the outer shell slot, thereby constraining the rotation of the outer shell relative to the middle shell as well as the inner shell. The hinge has a center of rotation governed by the rotation of the middle and outer shells.

In one embodiment, the middle and outer shells cannot each rotate simultaneously. A motion constraining element prevents rotation of the middle shell relative to the inner shell over a first flexion range. The arcuate length of the outer shell slot determines the first flexion range. Over this first flexion range the middle shell cannot rotate and only the outer shell rotates. A second flexion range is determined by the arcuate length of the middle shell slot and is continuous, but non-overlapping, with the first flexion range. Over this second flexion range the middle shell can rotate relative to the inner shell, but cannot rotate relative to the outer shell.

The motion constraining element can use any means known in the art that constrains rotation of one shell while permitting rotation of a second shell. In one embodiment, this motion constraining element is a bulb rotatably connected to the circumferential edge of the middle shell. The bulb can comprise a stem having two ends, with one end of the stem rotatably connected to the middle shell and the other end non-rotatably connected to four orthogonal arms. One of the arms is designed to engage the inner shell. A second arm is designed to engage the outer shell. The third and fourth arms are designed to receive a force from the inner and outer shells, respectively, thereby rotating the bulb and transitioning from an inner shell engagement to an outer shell engagement, or vice versa. In this manner the middle shell is either engaged to the inner shell and not rotating as the outer shell rotates, or the middle shell is engaged to the outer shell so that the middle shell can rotate relative to the inner shell, but not the outer shell.

Any motion constraining element known in the art can be used in the hinges of the present invention. For example, a cover shell that comprises a cover shell slot that an outer shell protuberance tracks can also function as a motion constraining element wherein over a first flexion range the cover shell slot is shaped similarly to the outer shell slot, and over a second flexion range the cover shell slot is shaped similarly to the middle shell slot. In this manner, the outer shell slot can follow the path of the hinge's center of rotation with flexion (as shown by the center of rotation path in FIGS. 2(A)-(C)), thereby constraining the motion of each of the shells.

The relative placement of the co-axis, the arc angle, and position of the shell slots relative to the co-axis are dictated by the abnormal knee condition to be corrected including valgus or varus malalignment as well as PMRI or AMRI conditions. For example, the lateral hinge of a varus knee brace, as well as the medial hinge of the valgus knee brace, can have an outer shell slot that is an arc of between about 20° to 40°, more preferably between 25° to 35°, and most preferably approximately 30°, of a notional circle, centered on the middle-outer co-axis of rotation having a radius of curvature ranging from between 5 mm to 17 mm, more preferably 8 mm to 12 mm, most preferably approximately 10 mm. The arc length of the outer shell slot corresponds to the first flexion range. The outer shell slot is positioned anterior to the middle-outer shell co-axis so that during flexion the location of the hinge's center of rotation varies with flexion over the first flexion range and is constrained by tracking of the middle shell protuberance with the outer shell slot. The middle shell slot is an arc of between about 110° and 130°, more preferably between about 115° and 125°, most preferably approximately 120°, of a notional circle, centered on the inner-middle co-axis of rotation having a radius of curvature ranging from between 5 mm to 17 mm, more preferably 8 mm to 12 mm, most preferably approximately 10 mm. The arc length of the middle shell slot corresponds to the second flexion range, whose range begins at the end of the first flexion range. The middle shell slot can be positioned posterior to the inner-middle shell co-axis, when the leg is fully extended, so that the center of rotation location remains unchanged over the second flexion range.

Another embodiment of a hinge for use in a knee brace is a medial hinge of a varus knee brace. The outer shell slot can be an arc of between about 50° to 70°, more preferably between about 55° to 65°, and most preferably approximately 60°, of a notional circle, centered on the middle-outer co-axis of rotation having a radius of curvature ranging from between 5 mm to 17 mm, more preferably 8 mm to 12 mm, most preferably approximately 10 mm. The outer shell slot is positioned anterior to the middle-outer shell co-axis so that during flexion the location of the hinge's center of rotation varies with flexion over the first flexion range and is constrained by tracking of the middle shell protuberance with the outer shell slot. The middle shell slot is an arc of between about 80° and 100°, more preferably between about 85° and 95°, most preferably approximately 90°, of a notional circle, centered on the inner-middle co-axis of rotation having a radius of curvature ranging from between 5 mm to 17 mm, more preferably 8 mm to 12 mm, most preferably approximately 10 mm. The middle shell slot can be positioned proximal to the inner-middle shell co-axis, when the leg is fully extended, so that the center of rotation location varies with flexion over the second flexion range.

Also provided is a lateral hinge of a valgus knee brace. The outer shell slot can be an arc of between about 50° to 70°, more preferably between about 55° to 65°, and most preferably approximately 60°, of a notional circle, centered on the middle-outer co-axis of rotation having a radius of curvature ranging from between 5 mm to 17 mm, more preferably 8 mm to 12 mm, most preferably approximately 10 mm. The outer shell slot is positioned distal to the middle-outer shell co-axis so that during flexion the location of the hinge's center of rotation varies with flexion over the first flexion range and is constrained by tracking of the middle shell protuberance with the outer shell slot. The middle shell slot is an arc of between about 80° and 100°, more preferably between about 85° and 95°, most preferably approximately 90°, of a notional circle, centered on the inner-middle co-axis of rotation having a radius of curvature ranging from between 5 mm to 17 mm, more preferably 8 mm to 12 mm, most preferably approximately 10 mm. The middle shell slot can be positioned posterior to the inner-middle shell co-axis, when the leg is fully extended, so that the center of rotation location varies with flexion over the second flexion range.

In another embodiment, the knee hinge comprises four shells: an inner, middle, outer and cover shell. The inner, middle and outer shells are as discussed above except the outer shell also comprises an outer shell protuberance. The cover shell comprises a cover shell slot. The outer shell protuberance tracks the cover shell slot such that the center of rotation of the hinge is also constrained by the cover shell slot shape. In this embodiment, the interaction of the outer shell protuberance with the cover shell slot functions as a motion constraining element. As in the previously discussed hinge embodiments, the arcuate angle and relative position of the middle and outer shell slots, which in turn dictate the cover shell slot shape, can be manipulated so as to compensate for a particular abnormal knee condition.

The present invention also provides braces that correct tibia translation and rotational malalignment by generating a torque on the tibia. This torque can be generated by any means known in the art, including by an elastic strap or a hinged joint, or a combination of the strap and hinged joint. The brace is particularly useful for treating antero-medial rotatory instability (AMRI) by applying a force on the anterior aspect of the medial tibia, resulting in a torque on the tibia that rotates the knee in an internal direction during flexion. The brace is also useful to treat postero-lateteral rotatory instability (PLRI) by applying a force on the posterior aspect of the lateral tibia causing an internal rotation force on the tibia during flexion. The knee brace can comprise one or two of the hinges of the present invention.

In one embodiment, the knee brace corrects a varus knee. In another embodiment the knee brace corrects a valgus knee. In addition, because most valgus knees are involved with PLRI, and most varus knees are involved with AMRI, the hinges and knee braces of the present invention are also applicable for correcting these abnormalities. For both embodiments, the knee brace comprises a thigh and tibial cuff having a medial, lateral and anterior portion. A proximal lateral arm and a distal lateral arm connect to the lateral thigh and lateral tibial cuff, respectively. A lateral hinge links the proximal and distal lateral arms. A proximal medial arm and a distal medial arm connect to the medial thigh and medial tibial cuff, respectively. A medial hinge links the proximal and distal medial arms. Posterior proximal and posterior distal belts connect the proximal and distal arms, respectively. Proximal and distal elastic bands can attach to the lateral and medial portions of the thigh and tibial cuffs, respectively. Means to secure the thigh cuff to a wearer's thigh the tibial cuff to the wearer's tibial shank can be of any means known in the art, including a buckle and strap system, a velcro system, or any combination of the two, for example.

A valgus-correcting knee brace can comprise a medial hinge that generates an unloading force on the medial compartment of the valgus knee and corrects the internal rotation of the tibia during flexion.

A varus-correcting knee brace can comprise a medial hinge that generates an unloading force on the lateral compartment of the valgus knee and corrects the internal rotation of the tibia during flexion.

The present invention also provides methods for treating knee pathology, including an osteoarthritic or osteoarthritic-prone knee. The method comprises application of a rotational force to the tibia during flexion to correct the abnormal tibial rotation by a pair of hinges. The hinges have a variable hinge length, dependent on flexion, and are located medial and lateral to the knee, such that an off-loading force can also be applied to the knee. Application of both forces during repeated flexion/extension cycles can correct abnormal knee rotation and can minimize the likelihood of osteoarthritis and/or osteoarthritic symptoms. These forces can be generated by paired hinges of the present invention, wherein the center of rotation of each hinge varies as a function of flexion. In addition, use of multiple shell slots and shell protuberances to track each of the shell slots permits the center of rotation location to vary as a function of flexion, wherein the function can be different for a first flexion range (tracking of a middle shell protuberance with an outer shell slot) and a second flexion range (tracking of an inner shell protuberance with a middle shell slot). The medial and lateral hinges can each also have a different center of rotation location as a function of flexion. Any of the hinges or braces of the invention can also be used for treating an injured or injury-prone knee.

BRIEF DESCRIPTION OF THE DRAWINGS

FIG. 1: Representations of tibial rotation as a function of flexion. In (A) the bold line labeled "normal path" represents the rotational alignment during flexion/extension in a normal knee, and the bold lines above and below the normal path represent the envelope of normal knee motion. The dashed lines labeled "Limited IR" and "Increased ER" represent the maximum internal rotation (IR) or external rotation (ER) rotation caused by accessory motion, and represents the envelope of the abnormal knee motion. When the leg is fully extended, the tibia cannot rotate; as the leg is flexed from extension, accessory motion increases to a relatively constant level beyond 30° flexion. The dotted "ER deviated path" line represents the natural path of the knee with rotational malalignment as a function of flexion in an abnormal knee. As shown by the dashed lines, the envelope of motion is shifted toward external rotation throughout flexion. There is also a diminished screw-home movement and a slight loss of extension in the abnormal knee. (B) A plot of the rotational alignment during flexion/extension in an abnormal knee that uses the present invention to correct rotational alignment during repeated flexion/extension cycles. The circular region shaded gray represents the knee position where the articular surface suffers excessive shear and compressive forces during standing activities when the leg is extended under the rotational malalignment.

FIG. 4: A diagram of a hinge that can be a lateral hinge of a varus knee brace or a medial hinge of a valgus knee brace.

FIG. 5: A diagram of a hinge that can be a medial hinge of a varus knee brace.

FIG. 6: A diagram of a hinge that can be a lateral hinge of a valgus knee brace.

FIG. 8: (A) Diagram of the motion constraining element of FIG. 7 showing the bulb and shell interaction at a flexion angle wherein shell rotation transitions from the outer to middle shells (B) and from the middle to outer shells (C).

FIG. 10: A diagram of an exemplary knee brace from an: (A) anterior view; (B) posterior view; (C) lateral view; and (D) medial view.

DETAILED DESCRIPTION OF THE INVENTION

Figure 2A:
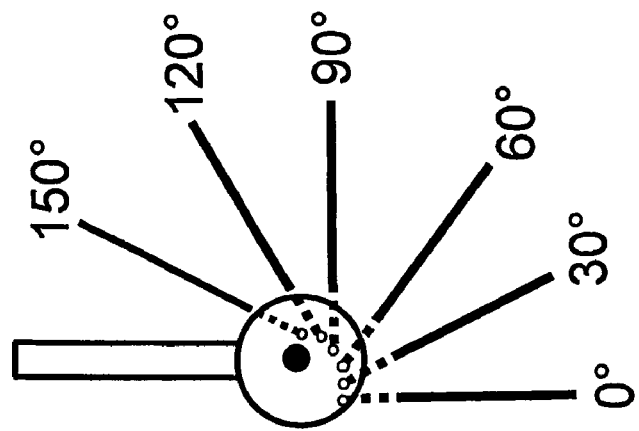
FIG. 2: A diagram of three exemplary hinge designs wherein the location of the center of rotation is a function of flexion. Shown is a fixed rectangular element representing the femoral arm and the bold/dash lines represent the tibial arm over a flexion range incrementing from 0° to 150° in 30° steps. (A) is an exemplary embodiment of a lateral and medial hinge for the varus and a valgus knee, respectively. (B) is an exemplary embodiment of a medial hinge for the varus knee. (C) is an exemplary embodiment of a lateral hinge for the valgus knee. Pairing the hinges of (A) and (B) can create an internal rotation as the knee flexes, and can apply a distraction force so as to separate the medial compartment as the leg extends. Pairing the hinges of (A) and (C) can also create an internal rotation as the knee flexes, and can apply a distraction force so as to separate the lateral compartment as the leg extends.

All references cited herein are hereby incorporated by reference to the extent not inconsistent with the disclosure herewith. As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

Although the description herein contains many specificities, these should not be construed as limiting the scope of the invention but as merely providing illustrations of some of the presently preferred embodiments of the invention. For example, thus the scope of the invention should be determined by the appended claims and their equivalents, rather than by the examples given.

The embodiments of the present invention are used to treat a variety of physical conditions or pathologies wherein there is a varus or valgus malalignment, and corresponding excessive rotation, of the knee. "Rotational alignment" is used to describe the amount the tibia is circumferentially rotated. The rotational alignment of the tibia varies with flexion and extension. Rotational alignment can be described in terms of the direction of the foot, in a locked position, with the knee. When the foot and knee line up, the knee is rotationally aligned. When the tibia is rotated such that the foot rotates in an outward direction from the body's center, the knee (or tibia) is "externally rotated." If the tibia rotates in the other direction, toward the inside of the body, the knee is "internally rotated." "Flexion" or "extension" refers to the angle defined by the tibia and femur. A straight leg is a fully extended leg and a leg that is going from straight to flexed is undergoing flexion. A leg that is being straightened from flexion is said to be approaching extension.

A component of abnormal rotational alignment is translation of the tibia, relative to the femur. The ligaments normally restrict tibial translation, but if any are damaged the tibia may excessively move, relative to the femur, forward (anterior), backward (posterior), inside (medial), outside (lateral) away from (distal) and/or towards (proximal). The tibial rotational malalignment and translation should be corrected simultaneously to reduce and correct abnormal loading of the meniscus that cushions the tibia from the femur. Some translation of the tibia, relative to the femur is normal. For example, it has been estimated that the tibia normally translates 8 mm anterior as the leg flexes from full extension through 25°. U.S. Pat. No. 4,723,539.

The tibia is typically both externally rotated and laterally translated in the varus (bowlegged) knee. This positioning of the tibia causes an abnormal pressure distribution over the tibia. In particular, the unbalanced pressure in the varus knee causes compression of the medial compartment of the knee. The maximum pressure on the medial compartment occurs with standing and the condition progressively worsens under continued rotational malalignment during gait. The present invention prevents this worsening by simultaneously correcting tibial translation and abnormal rotational alignment. This correction occurs gradually by applying corrective forces throughout repeated flexion motions.

As used herein, "abnormally loaded" refers to a force on the medial compartment of the knee that is different from the force on the lateral compartment of the knee. This results in an unbalanced loading of the tibia; "abnormally-loaded" or "unhealthy" knee is used to describe such a condition. Such imbalance causes the compartment that experiences the greater force to compress relative to the opposite compartment that experiences a lower force, especially during gait when the leg approaches and becomes fully extended. The excessive force on one side of the knee causes pain and discomfort and is associated with OA. A knee whose medial and lateral compartments experience similar forces during standing is said to be a "normally-loaded" or "healthy" knee.

Rotational alignment for healthy knees and abnormally-loaded knees can be plotted as a function of flexion (See FIG. 1(A)). Rotational alignment varies with the amount of flexion (FIG. 1). Flexion is a measure of the angle formed between the tibia and a straight line drawn along the longitudinal axis of the femur extended distally. Thus, an angle of 0° represents the straight leg and 90° the leg bent at a right angle. A normal knee joint can extend the leg slightly beyond 0° and is shown by the portion of the curve left of the y-axis. During gait, the knee joint cyclically goes from extended to flexed and back to extended. FIG. 1(A) is a graph of rotational alignment for a healthy knee and an abnormal knee as the leg bends from fully extended to 90° flexion. The normal knee path is shown by the solid line labeled "normal path" that follows the x-axis at higher flexion. The knee path for an abnormal knee with excessive external rotation is given by the dotted line labeled "ER deviated path." The tibia normally becomes progressively externally rotated within 20° to 30° of terminal extension; as the leg flexes from extension, the knee becomes rotationally aligned. There is significant accessory internal/external rotation and abduction/adduction motion when the knee joint is flexed more than 30°. However, below 30° flexion accessory motion is increasingly constrained and at terminal extension there is no accessory motion. The solid lines above and below the solid line labeled "normal path" in FIG. 1 represent this accessory motion for a healthy knee. The region of the graph between the limit lines is called an "envelope" of knee motion. Note that in a healthy knee, when fully extended, the tibia is unable to rotate. In other words, there is no accessory motion in the fully extended leg. The longer dashed lines represent the envelope for the unhealthy knee. In this unhealthy knee example the envelope is shifted toward external rotation so that there is reduced internal rotation and excessive external rotation.

"Healthy knee" is also used to describe a knee whose rotational alignment as a function of flexion follows the "normal path" shown in FIG. 1(A). In a healthy knee the tibia is not abnormally or excessively rotated with respect to the femur. In an abnormally-loaded knee, however, the tibia is abnormally rotated and the rotational alignment as a function of flexion does not follow the normal path shown in FIG. 1(A). Instead, because of rotational malalignment, the knee rotation path can change as shown in FIG. 1(A), where the knee remains externally rotated throughout flexion, as is often found in knees with antero-medial rotatory instability (AMRI) and/or postero-lateteral rotatory instability (PLRI), and has a slight loss of extension. Excessive external rotation at extension causes an excessive shear stress and an unbalanced load on the knee, aggravating OA.

There are different underlying bases for a changed rotation path including soft-tissue imbalance such as tightness of the iliotibial band (ITB), with or without underlying rotational instabilities such as AMRI, or PLRI, both of which cause an excessive external rotation. A knee joint with excessive external rotation and limited internal rotation has "external rotation contracture" and is shown in FIG. 1(A) as a general upward shift in the curves. The loss of increasing external rotation as the leg approaches full extension (within approximately 20° to 30°) is called a "diminished screw-home motion."

Both varus (bow-leggedness) and valgus (knock-kneed) deformities involve an external rotation and a lateral translation of the tibia. In both the varus and valgus knee there is commonly an external rotation contracture. Initial external rotation contracture at younger ages may not cause severe damage to the knee joint because the articular cartilage is soft and smooth; but it can progressively aggravate the joint surface with age because an abnormal motion due to the contracture is continuously repeated during the gait cycle. The result is a gradual loss toward internal rotation as shown in FIG. 1(A). The initial stage of rotational contracture is caused by the anatomical characteristics of the bones and tightness of the soft tissue around the joint. Soft tissue tightness or adhesion caused by inflammation of the joint or bursitis aggravates this contracture and further increases the rotational malalignment. Studies have shown that the screw-home movement is reduced or abolished in abnormal knee kinematics because of external rotation contracture. It is the repeated flexion/extension cycles of the knee under this rotational malalignment that causes an abnormal loading pattern and shear stress on the surface of the tibia.

To correct the excessive external rotation, a corrective force that internally rotates the tibia can be applied during flexion, rather than at extension, because the tibia is constrained from rotating when the leg is extended. FIG. 1(B) shows this concept of alignment correction by repeated flexion cycles with continuous application of internal rotation torque during knee flexion. An internal rotational torque is applied to the tibia by the brace during flexion, by any means known to the art, while stabilizing the femur, so that instead of following the path labeled "abnormal," the path follows the dashed line from the point labeled with a "1" to the point labeled with a "2". During the return phase from flexion to extension, under a continued internal rotational torque, the path goes from the point labeled with a "2" to the "3". The knee returns to the normal path with repeated cycles of flexion/extension under the applied rotational torque. For diagram clarity, only two such cycles are diagrammed (shown by the dashed lines). In practice, such correction will take, depending on the severity of OA, malalignment and soft tissue imbalance, on the order of tens of repetitions (if the motion is repeated precisely) for temporary correction, and on the order of thousands to tens of thousands of repetitions for more permanent correction.

A force can be applied to the tibia during flexion, resulting in a torque on the tibia, by any means known to the art. For example, U.S. Provisional Application No. 60/529,139 filed Dec. 12, 2003, discloses various means, alone or in combination, including a spiral strap, a single-hinge joint and a double-hinged joint, that can be used alone or in combination to generate such a force, and is hereby incorporated by reference. However, such a force on the tibia is preferably generated by a knee brace having a pair of hinges located medially and laterally, with respect to the knee joint, to continuously apply rotational force or torque to the knee during flexion (see FIG. 10), wherein the hinges provide a means for controlling the location of the center of rotation of each hinge.

Without limiting the claimed invention to any particular theory, in early stage OA when there is no significant radiographic deformity, the knee has external rotation contracture in flexion. Continued repetition of this external rotation contracture causes an abnormal loading pattern and stresses on the knee joint and progressive worsening of OA. By correcting the external rotation contracture during flexion, the effect of OA can be abolished or minimized by balancing the load on the medial and lateral compartments. Faster, more permanent results are expected with rehabilitative training involving weight and resistance equipment, whereby the tibia is rotated into correct alignment, under a counter-balancing force, as disclosed in U.S. Provisional Application No. 60/543,515, filed Feb. 10, 2004, hereby incorporated by reference.

As used herein, "center of rotation" refers to a point in the knee brace hinge that does not move as the tibial arm extends and flexes, about which the rest of the hinge rotates. Recent studies show that the knee joint also contains a center of rotation about which the tibia rotates, referred to as the "geometrical axis" or the "cylindrical axis" and is generally located transverse to the femoral condyles. The hinges of the present invention comprise multiple shells, shell slots, and protuberances that track the shell slots, so that the location of the center of rotation varies as a function of flexion, and the variation can be manipulated and controlled. The inner shell is centered on the cylindrical axis. The variability in the location of the center of rotation with flexion permits the physical forces exerted on the knee joint to be varied as a function of flexion. In one embodiment of the invention, transitioning the location of the center of rotation from one shell pair to another shell pair, at a specific flexion value, permits greater control of the physical forces exerted on the knee joint. In general, valgus or varus corrections can be achieved by lengthening of one hinge and shortening the other hinge, thereby unloading the compressive force on the particular knee compartment, when the knee is in extension between zero and thirty degrees (U.S. Pat. No. 5,277,698). Simultaneous to this unloading, use of suitably paired hinges of the present invention permits the tibia to be appropriately rotated and generate suitable compression/distraction or abduction/adduction motion during flexion. Distraction is a force that can separate the femur relative to the tibia, thereby relieving or reducing compression of the relevant compartment. In such a manner, methods are provided for treating various knee pathologies, including OA or OA-prone knees. Knee pathology refers to any degenerative disease of the knee and can include traumatic injury, meniscal injury, articular cartilage and ligament injury as well as abnormalities arising from rheumatoid arthritis. In a preferred embodiment, the method is for treatment of OA or OA-prone knees.

FIG. 2 shows the location of the center of rotation as a function of flexion for three hinge embodiments. These paths are also referred herein as a "variable center of rotation." FIG. 2 shows: (1) the non-moving femoral arm or femoral shell, represented by a rectangle attached above the circular hinge; (2) a tibial arm or tibial shell flexing from 0° to 150° represented by the solid lines; and (3) the center of rotation position as a function of flexion, relative to the cylindrical axis. The dashed lines demonstrate the path of the tibial shell if the tibial shell were to extend through the hinge and is helpful to show the location of the center of rotation for different flexion values. FIG. 2(A) is one embodiment for a lateral or a medial hinge for use in a varus or valgus-correcting knee brace, respectively. For the fully extended leg (flexion equals zero), the center of rotation is anterior and proximal to the cylindrical axis. The center of rotation for this hinge varies from 0° to 30°, but for flexion values greater than 30°, the center of rotation location is fixed at the cylindrical axis.

Figure 2B:
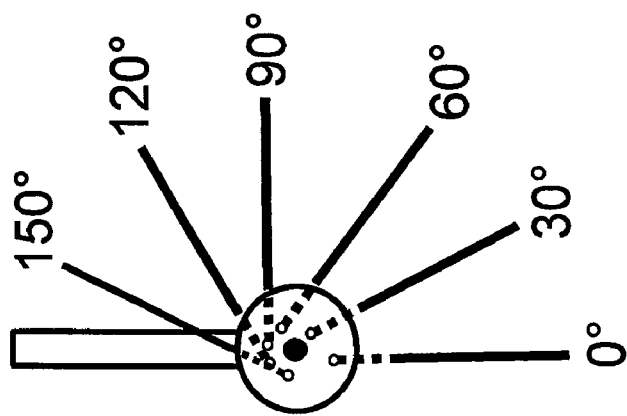

FIG. 2(B) shows one embodiment for a medial hinge for a varus-correcting knee brace, used in combination with the lateral hinge shown in FIG. 2(A). For this hinge, the center of rotation's location varies continuously with flexion. It moves from a distal and slightly anterior position at zero degree flexion, to a posterior and proximal position at intermediate flexion, to an anterior position at flexion values of approximately 150°. The combination of the hinges in FIGS. 2(A) and 2(B) achieves unloading of the medial compartment in extension by lengthening the medial hinge and shortening the lateral hinge as the leg extends. Simultaneously, this hinge pair can internally rotate the tibia by translating the medial tibial arm posteriorly while the location of the center of rotation in the lateral hinge is unchanged for flexion values greater than approximately 30°.

Figure 2C:
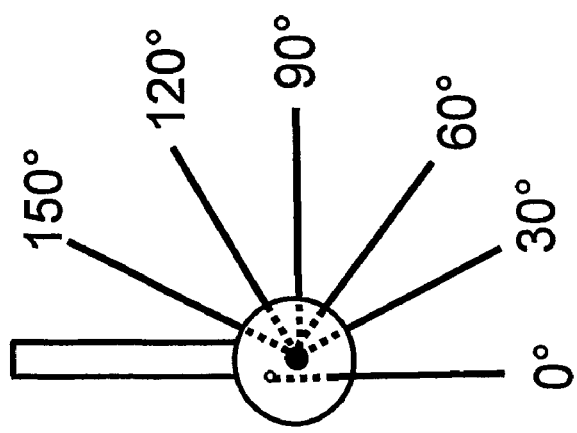

FIG. 2(C) shows one embodiment of a lateral hinge for use in a valgus-correcting knee brace, used in combination with the medial hinge shown in FIG. 2(A). The center of rotation's position in this hinge varies continuously as a function of flexion. In contrast to the hinge in 2(B), the position generally remains distal to the cylindrical axis. When the leg is fully extended the location is distal and anterior to the cylindrical axis. As the leg flexes, the center of rotation location moves in a posterior direction and for flexion greater than about 90° the center of rotation location is posterior to the cylindrical axis. The location begins to move in a proximal direction for flexion greater than about 60°. The combination of the hinge in FIG. 2(A) (placed medial to the valgus knee), and the hinge in FIG. 2(C) (placed lateral to the valgus knee), results in unloading of the lateral compartment of the knee by lengthening of the lateral hinge and shortening of the medial hinge in extension. Simultaneously, internal rotation of the tibia during flexion is achieved by translation of the lateral tibial arm anteriorly while the location of the center of rotation in the medial hinge is unchanged for flexion greater than about 30°.

As used herein, center of rotation location as a function of flexion refers to the path of a hinge's center of rotation with flexion as shown, for example, in the three hinge examples of FIG. 2. One of ordinary skill in the art will recognize that this function can be of any form, and is not constrained by the three embodiments given in FIG. 2. The particular function will be governed by the knee condition which dictates the location, magnitude and type of force to be applied at any given flexion value.

The hinges of this invention are not restricted to knee braces, and they can also be incorporated into hinges for other uses including, for example, elbow joints or in mechanical devices, including robotics, where it is useful to simulate joint motion.

"Rotatably engaged" refers to a shell having a rotation relative to another shell that is determined by the interaction of the shell slot with the shell protuberance attached to the other shell. The shell protuberances, one located on the inner shell and another on the middle shell, can be of any type, including pins, bolts, screws, rivets, or the like, so long as the protuberance can track the slot. "Track" or "tracking" is used to refer to the interaction of the protuberance with the shell slot. Thus, a shell's rotation and translation, if any, is constrained by the track of the protuberance along the shell slot. The term "shell slot" is used broadly herein. It is any means wherein, in combination with the protuberance, the shell's rotation is constrained. Thus, shell slot includes channels that are bored completely through the shell, as well as channels that are machined only partway through the shell, so long as the protuberance can track the slot without disengaging or getting stuck.

The middle and outer shells can rotate, but the rotation is constrained by the interaction with the associated protuberance. A shell that is rotating has a co-axis, which is a center of rotation that is not rotating, with the shell upon which the engaging protuberance is located. Optionally, this co-axis is rotatably anchored between the rotatably engaged shells by any means known in the art, including by a screw, pin, bolt, rivet, or the like, so long as the shell can rotate.

In one embodiment, the hinges of the present invention comprise three shells (FIGS. 3-6). The hinge shells can be concave-shaped, preferably in the shape of a sphere segment, with the concavity facing inward toward the knee joint. The shells are composed of any material known in the art of knee braces (see U.S. Patent Application Publication No. 2004/0054311, hereby incorporated by reference), so long as the hinge is capable of withstanding and generating a load on a knee joint. The material should impart sufficient rigidity to the hinge and can include various metals and composites such as graphite, plastic, or resin composites. Although the shell dimensions can be of various sizes, the shell radius is preferably between about 4 cm to about 5 cm in radius and each shell within the hinge can have a radius that is the same or slightly different than the radii of the other shells.

Figure 3A:
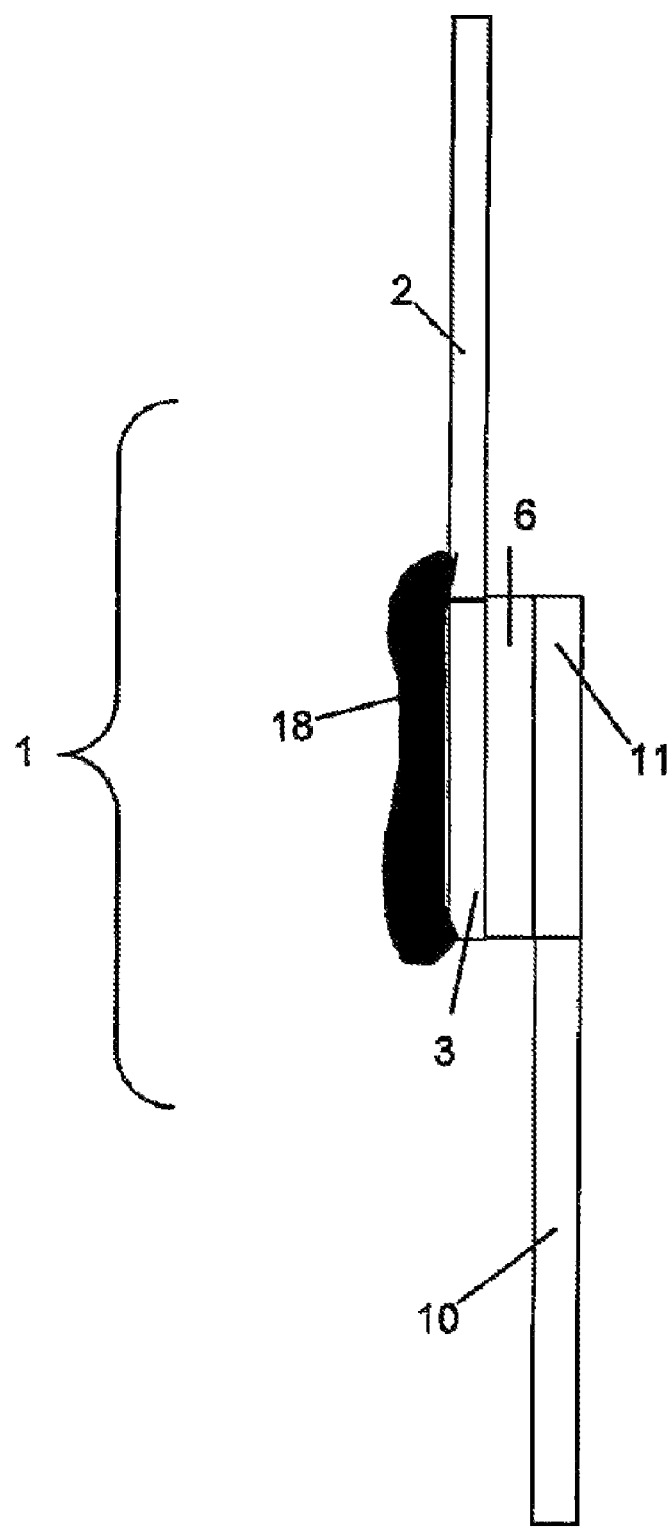
FIG. 3: (A) is a cross-section of a three-shell hinge. (B) is an exploded perspective view of a three-shell hinge.
Figure 3B:
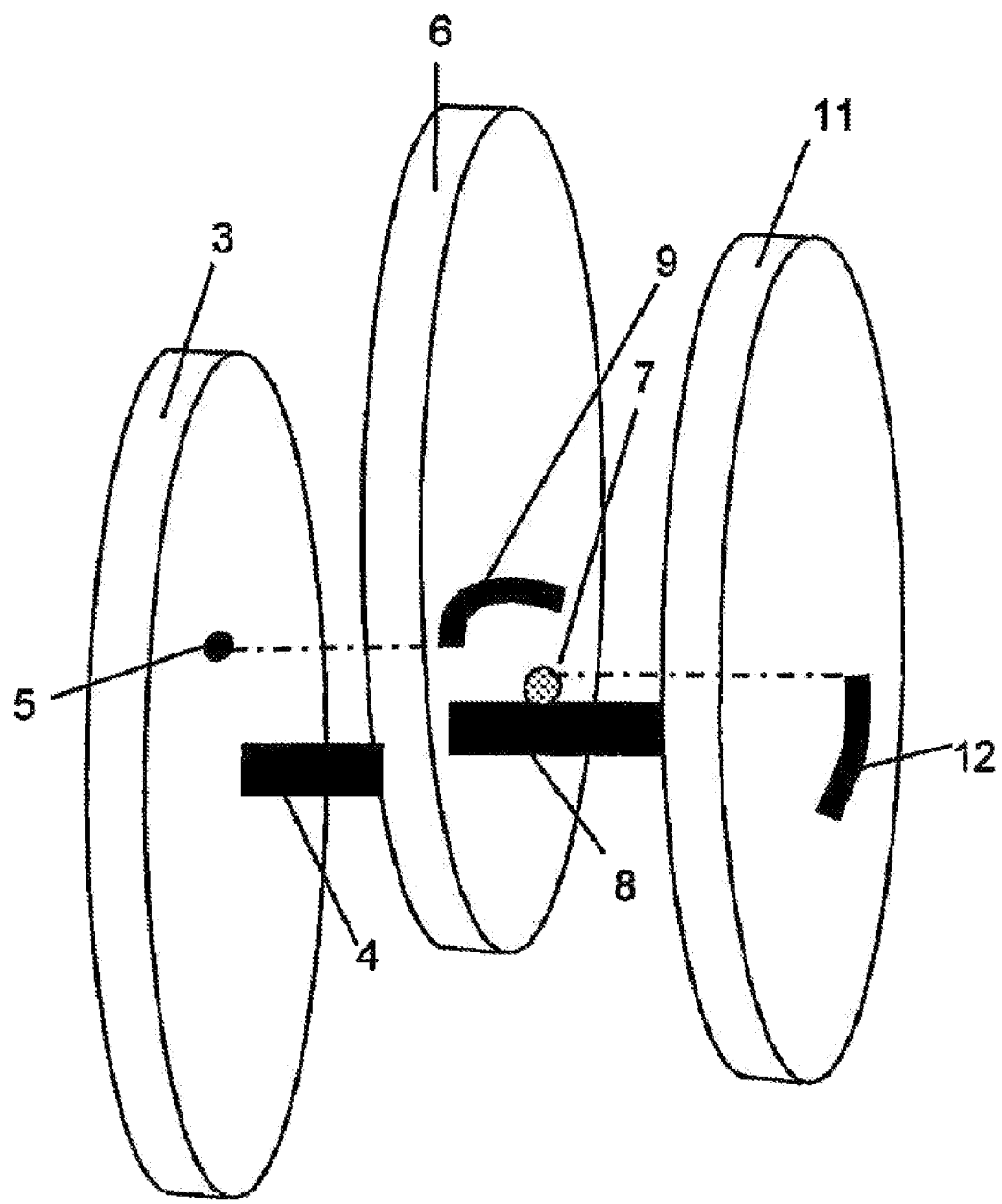

FIG. 3 shows a three-shell hinge with a cross-sectional view in (A) and a perspective view in (B). There is an inner shell 3 closest to the knee, a middle shell 6 and an outer shell 11, furthest from the knee. Also show is an optional pad 18 used to cushion the hinge against the knee joint. The inner shell 3 can be rigidly connected to a proximal arm, also called a femur shell or femur arm, 2. Depending on whether the hinge is medial or lateral, element 2 corresponds to element 52 (proximal medial arm) and 50 (proximal lateral arm) of FIG. 10. The outer shell 11 can be rigidly connected to the distal arm, also called a tibial shell or tibial arm, 10. Depending on whether the hinge is medial or lateral, element 2 corresponds to element 56 (distal medial arm) and 54 (distal lateral arm) of FIG. 10. Optionally, elements 2 and 10 comprise a one-piece mold with the inner shell 3 and the outer shell 11, respectively. Alternatively, arms 2 and 10 can be separate pieces that can be rigidly connect to the shell by any means in the art including fasteners, screws, glue and the like. The exploded perspective view in FIG. 3(B) shows how the shells are rotatably engaged. Inner shell 3 and middle shell 6 have a co-axis 4, about which middle shell rotates. Inner shell protuberance 5 engages and tracks middle shell slot 9. Thereby, middle shell 6 rotation is constrained by the location of the inner-middle shell co-axis 4 and the shape and location of the middle shell slot 9. The middle and outer shells 6 and 11 are likewise rotatably connected about middle-outer shell co-axis 8. Middle shell protuberance 7 engages and tracks outer shell slot 12. Optionally, the hinge includes bushings shaped to match the shape of the shells, to reduce friction between the rotating shell and non-rotating shell.

In one embodiment, the outer shell and middle shells cannot simultaneously rotate. The middle shell 6 rotates, relative to the inner shell 3 but not to the outer shell 11, over a first flexion range, and the outer shell 11 rotates relative to the middle shell but not the inner shell 3, over a second flexion range. The two flexion ranges are continuous, but non-overlapping. The specific ranges are variable, dependent on the knee pathology to be corrected. One advantage of the present hinges is that they are customizable to individuals and the two separate rotation ranges permit manipulation of the hinge's center of rotation to generate precise rotational forces on the tibia and generate off-loading forces, as a function of flexion.

The invention may be further understood by the following non-limiting examples. The following examples are provided for illustrative purposes only, and are not intended to limit the scope of the invention as claimed herein.

To correct a varus knee, paired hinges, as shown in FIGS. 2(A) and (B) can be employed. The lateral hinge of FIG. 2(A) and the medial hinge of FIG. 2(B) correspond to the hinges shown in FIGS. 4 and 5, respectively. When the leg approaches extension, the lateral hinge length is greater than the medial hinge length resulting in unloading of the medial compartment. FIGS. 4(A), (B) and (C) show the inner 3, middle 6 and outer 11 shells, respectively, that comprise the lateral hinge and is a different view than in FIG. 3. The inner shell 3 can be connected to a proximal lateral hinge arm 2 that connects the hinge to the lateral thigh cuff 34 shown in FIG. 10. The inner shell can be rigidly fixed relative to the thigh by 2 (52) so that the inner shell does not rotate. The middle shell is rotatably connected to the inner shell and rotates about an inner-middle shell co-axis 4. The rotation is constrained by the interaction or tracking of the inner shell protuberance 5 with the middle shell slot 9. Optional element 14 is shown to assist in distinguishing the amount middle shell 6 rotates.

The outer shell 11 is rotatably connected to the middle shell 6 and rotates about a middle-outer shell co-axis 8. The rotation is constrained by the interaction or tracking of the middle shell protuberance 7 with the outer shell slot 12. The outer shell 11 can be connected to a distal lateral hinge arm 10 (54, 56) that connects the hinge to the distal tibial cuff 44. As the leg flexes (e.g. the tibia rotates about the cylindrical axis) the outer shell rotates correspondingly. FIGS. 4(D) and (E) demonstrate the rotation of the outer shell relative to the middle shell and rotation of the middle shell relative to the inner shell, respectively. Over a first flexion range, only the outer shell rotates relative to the middle shell, as demonstrated in FIG. 4(D). FIG. 4(D) is one embodiment where the first flexion range is from 0° to 30°. FIG. 4(D) is a side view of the rotation interaction of the middle shell and outer shell. At extension, the middle shell protuberance 7 is at the distal end of outer shell slot 12. At 30° flexion the middle shell protuberance 7 is at the proximal end of outer shell slot 12. Because the middle-outer shell co-axis is not centered on the middle and outer shells, the center of rotation varies with flexion, over the first flexion range. As shown in FIG. 4(E), for a second flexion range the middle shell 6 rotates relative to the inner shell 3. At 30° flexion the inner shell protuberance 5 is at one end of the middle shell slot 9, and as leg flexion increases, the middle shell 6 rotates about the inner-middle shell co-axis 4 so that the inner shell protuberance tracks the middle shell slot 9. In this embodiment, the middle shell can rotate up to a maximum of 150° and the interaction of the inner shell protuberance 5 with the other end of the middle shell slot 9 prevents further flexion. Because the inner-middle shell co-axis is centered with respect to the inner and middle shells, the center of rotation location remains unchanged over the second flexion range. The center of rotation for this hinge varies from 0° to 30° flexion, and remains unchanged and centered on the cylindrical axis from 30° to 150° flexion, as shown in FIG. 2(A).

FIG. 5 shows one embodiment of a medial hinge that can be used to correct a varus knee and corresponds to the hinge shown in FIG. 2(B). As shown in FIGS. 5(B) and (C) the shell slots 9 and 12 and middle-outer shell co-axis 8 positions have changed (compare to FIGS. 4(B) and (C)). In addition, the length of the middle shell slot 9 has increased so that the first flexion range extends to 60° and the second shell slot length has correspondingly decreased so that the second flexion range is 60° to 150°. Such shell slot and co-axis configurations result in the center of rotation continuously changing with flexion throughout both flexion ranges as shown in FIG. 2(B). Placing the hinge in FIG. 4 lateral to the knee, and the hinge in FIG. 5 medial to the knee, generates appropriate forces to correct varus-type deformities by internally rotating the tibia during knee flexion and by unloading the medial compartment during knee extension.

To correct a valgus knee, paired hinges, as shown in FIGS. 3(A) and (C), can be employed. One embodiment of the medial hinge of a valgus-correcting knee brace utilizes the hinge shown in FIG. 2(A) and FIG. 4, medial to the knee. One embodiment of a lateral hinge for use in a valgus-correcting knee brace is shown in FIG. 6. FIG. 6 corresponds to the hinge shown in FIG. 2(C). The co-axis and the shell slot locations are located so that the lateral compartment is unloaded in extension and internal tibial rotation during flexion is generated by translation of the lateral tibial arm anteriorly while the center of rotation in the medial hinge is fixed on the cylindrical axis.

Manipulating the position of the co-axis relative to the center of the shells, the length of the shell slot, and the radius of curvature of the arcuate shell slots permit precise control of the center of rotation location as a function of flexion. In particular, the locations of (1) the inner-middle shell co-axis, relative to the middle shell; (2) the middle shell slot; (3) the middle-outer shell co-axis; and (4) the outer shell slot, dictate the location, direction and magnitude of the force exerted on the tibia during flexion. The radius of curvature of the shell slots can be generally on the order of the radius of the femoral condyle of the wearer. (e.g. approximately 11 mm, see U.S. Pat. No. 4,723,539). The radius of curvature can be 5 mm to 17 mm, more preferably 8 mm to 11 mm, and most preferably approximately 10 mm. The radius of curvature, however, is not constrained by the geometry of the shells. The radius of curvature is constrained by the location of the co-axis of rotation because the shell slot is centered on the co-axis of rotation. The radius of curvature of the shell slots is, however, dictated by the type and degree of knee malalignment and the physical force necessary to correct such malalignment. Similarly, the flexion angle at which rotation transitions from the outside shell to the middle shell is also variable and controlled by the arcuate length of the shell slots. Flexion limits can be controlled by machining different arcuate segment slot lengths or by the use of stoppers placed in the slot at an appropriate point. The stopper can be a screw or rivet or any other device mounted within the slot to limit travel of the protuberance in the slot.

In AMRI, the medial tibial plateau is excessively translated in an anterior direction; this causes an excessive external rotation of the knee throughout flexion. To correct this external rotation, a torsional force in an internal direction is generated during the swing phase of the gait cycle, while limiting the external rotation, via a brace. Correction of rotational alignment during swing phase ultimately corrects the abnormal loading pattern during the stance phase (FIG. 1(B)). In addition, means well known in the art can be incorporated to correct more serious knee conditions involving valgus or varus deformities (e.g. off-loading braces as described in U.S. Pat. No. 5,277,698). The hinges and knee braces of the present invention can be used to simultaneously provide off-loading via a three point pressure-unloading type mechanism, similar to the UNLOADER® (Generation II) brand knee braces and, with physiological level of forces, rotate the tibia into a normal rotational alignment.

A knee with AMRI has an excessive anterior translation of the medial tibial condyle with an associated increase in pressure on the anteromedial aspect of the tibia and external rotation of the knee. An internal torque during flexion (0° to 30°) is applied by any means known to the art, including the hinges of the present invention. For example, U.S. Provisional Application 60/529,139 filed Dec. 12, 2003 shows the use of a strap that spirals around the knee joint to generate this force in extension. Alternatively, hinge joints can generate a similar force in knee flexion, as discussed in FIGS. 4-6. A posterior force on the medial aspect of the anterior tibia limits and corrects the displacement of the tibia and generates an inward-directed rotational torque on the tibia. This can be generated, for example by a lateral hinge of the type shown in FIG. 4 and a medial hinge of the type shown in FIG. 5.

During PLRI there is an excessive posterior translation of the lateral tibial plateau and an excessive external rotation of the knee throughout flexion. To offset the tibial translation, a force is applied to the posterior aspect of the lateral tibia during flexion FIGS. 6 and 7 of U.S. Provisional Application 60/529,139 filed Dec. 12, 2003 show the use of a strap and a hinge, respectively, to generate this force. In addition, the hinges and knee braces of the present invention can be used to generate this force. For example, a lateral hinge of the type shown in FIG. 6 and a medial hinge of the type shown in FIG. 4 can exert a force on the posterior aspect of the lateral tibia during flexion. This force limits the tibia displacement and generates an inward-directed torque, while limiting external rotation of the tibia.

As used herein, "first variable center of rotation" and "second variable center of rotation" refers to how the center of rotation for a first and second hinge, respectively, varies with flexion (see, e.g., FIG. 2). Each of the first and second function of flexion is further divided into two flexion ranges (see, e.g., FIGS. 4-6). A first flexion range is defined, for the medial hinge, by tracking of the medial hinge's middle shell protuberance with the medial hinge's outer shell slot. A second flexion range is defined, for the medial hinge, by tracking of the medial hinge's inner shell protuberance with the medial hinge's middle shell slot. The first and second flexion ranges are continuous and non-overlapping. The third flexion range is defined, for the lateral hinge, by tracking of the lateral hinge's middle shell protuberance with the lateral hinge's outer shell slot. The fourth flexion range is defined, for the lateral hinge, by tracking of the lateral hinge's inner shell protuberance with the lateral hinge's middle shell slot. The third and fourth flexion ranges are continuous and non-overlapping. In this manner, the variation of the center of rotation with flexion for each hinge can be different, with each hinge having different flexion range limits. The first flexion range can, but does not have to, equal the third flexion range, and the second flexion range can, but does not have to, equal the fourth flexion range.

The paired hinges can generate a rotational force on the knee joint by manipulating the relative positions of the center of rotation as a function of flexion. For example, in the varus knee brace, the cylindrical axis is always anterior to the center of rotation of the medial tibial arm over the second flexion range. This results in maintaining the medial side of the tibia in a relatively posterior position (relative to the cylindrical axis fixed with the femoral arm), thereby preventing AMRI. In another example, in a valgus knee brace, throughout the fourth flexion range the cylindrical axis is always posterior to the center of rotation of the lateral tibial arm. This results in maintaining the lateral side of the tibia in a relatively anterior position (relative to the cylindrical axis fixed with the femoral arm), thereby preventing PLRI.

Figure 7:
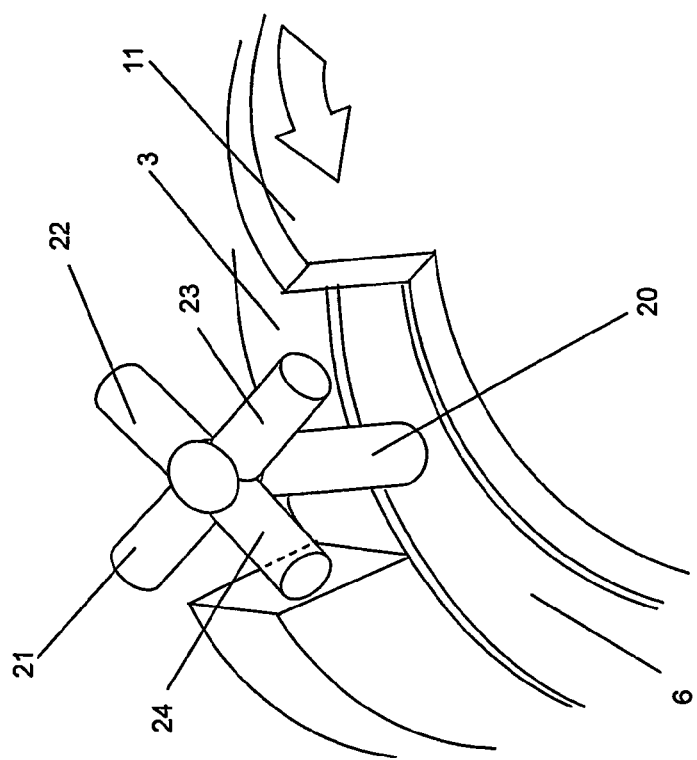
FIG. 7: A perspective diagram of one embodiment of a motion constraining element.

The outer shell and middle shell can be rotated independently by any means known in the art, including through the use of a motion constraining element. For example, FIG. 7 is one possible motion constraining element, whereby the outer shell rotates without the middle shell rotating, and the middle shell rotates relative to the inner shell but not relative to the outer shell. A rotatable bulb 20 is connected to the outer circumferential edge of the middle shell 6. The bulb comprises a stem 20 rotatably connected at one end to the middle shell 6 and four orthogonal arms 21, 22, 23, and 24 connected to the other end of the stem. The bulb can rotate in increments of 90°. Arm 21 is designed to engage with the outer shell 11 and arm 22 is designed to engage with the inner shell 3. The other two arms, 23 and 24 are designed to receive a force from the inner 3 and outer 11 shell, respectively, to rotate the bulb 90° so that arm 21 or 22 engage their respective shell. The term engage is used broadly to describe any interaction known in the art that results in the middle shell not rotating with respect to the shell arm 21 or 22 has engaged.

FIG. 8 is a schematic of how the rotatable bulb functions to ensure independent rotation of the shells. When the leg is fully extended, as in FIG. 8(A) the orthogonal arm 21 interacts with the inner shell such that the middle shell cannot rotate, as represented by the dashed oval 25. This interaction can occur by any means known in the art. For example, there can be an intimate interaction between the arm 21 and the inner shell 3 arising from a geometrical fitting between the arm and the shell. This fitting can occur via a shallow slot or indentation in the inner shell 3 in which the arm 21 fits. Alternatively, or in combination with, there could be a magnetic interaction between the arm and the shell such that the bulb rotatably fixes the middle shell relative to the inner shell. As shown in FIG. 8(A), over a first flexion range, the outer shell rotates freely, constrained by the tracking of the middle shell protuberance with the outer shell slot, while the inner and middle shell do not rotate. At the transition point between the first and second flexion range, however, the outer shell 11 impinges upon the orthogonal arm 23, generating a force sufficient to dislodge arm 21 from its engagement with the inner shell, thereby rotating the bulb stem 20 by 90°. The bulb can rotate such that arm 22 rotates and interacts with the outer shell 11. This interaction can also be by any means known in the art, so long as the interaction is sufficient such that the middle shell cannot rotate relative to the outer shell. Thus, over the second flexion range, both the outer and middle shell rotate relative to the inner shell. However, the outer and middle shells do not rotate relative to one another. The interaction can be mediated by, for example, a geometrical fitting between the arm 22 and outer shell 11, a magnetic interaction or a combination of the two.

FIG. 8(C) demonstrates the bulb motion when the second flexion range transitions to the first flexion range. The inner shell 3 impinges upon the orthogonal arm 24, generating a force sufficient to rotate the bulb 90° in a direction opposite to the direction when the transition was from the first flexion range to the second flexion range. Thus, over the first flexion range the middle and inner shells interact via arm 21, so that the outer shell rotates relative to the inner and middle shells, but the middle shell does not rotate relative to the inner shell.

Figure 9A:
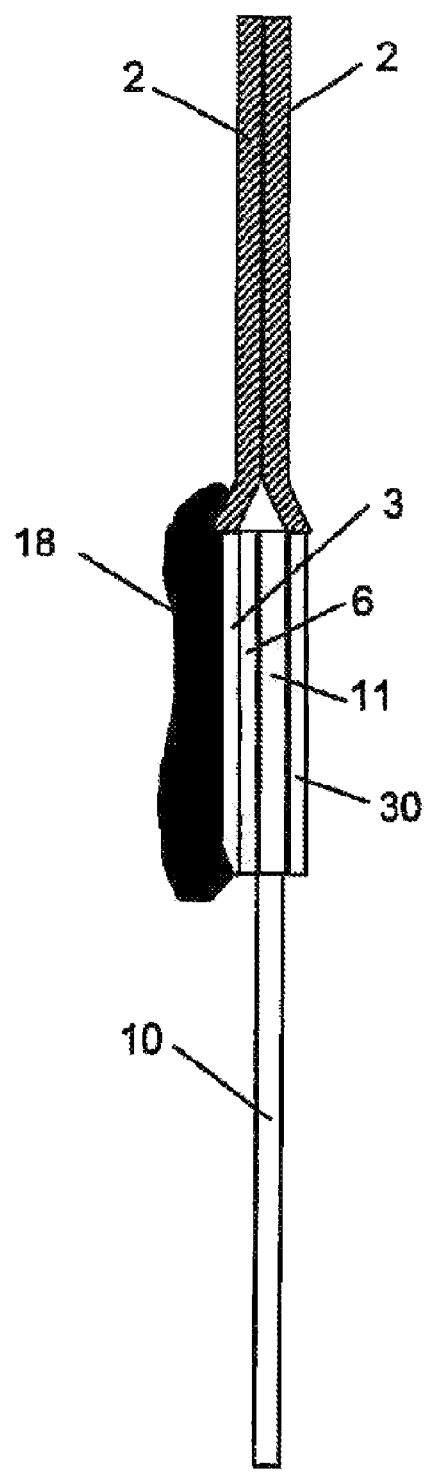
FIG. 9: A diagram of a hinge comprising four shells.
Figure 9B:
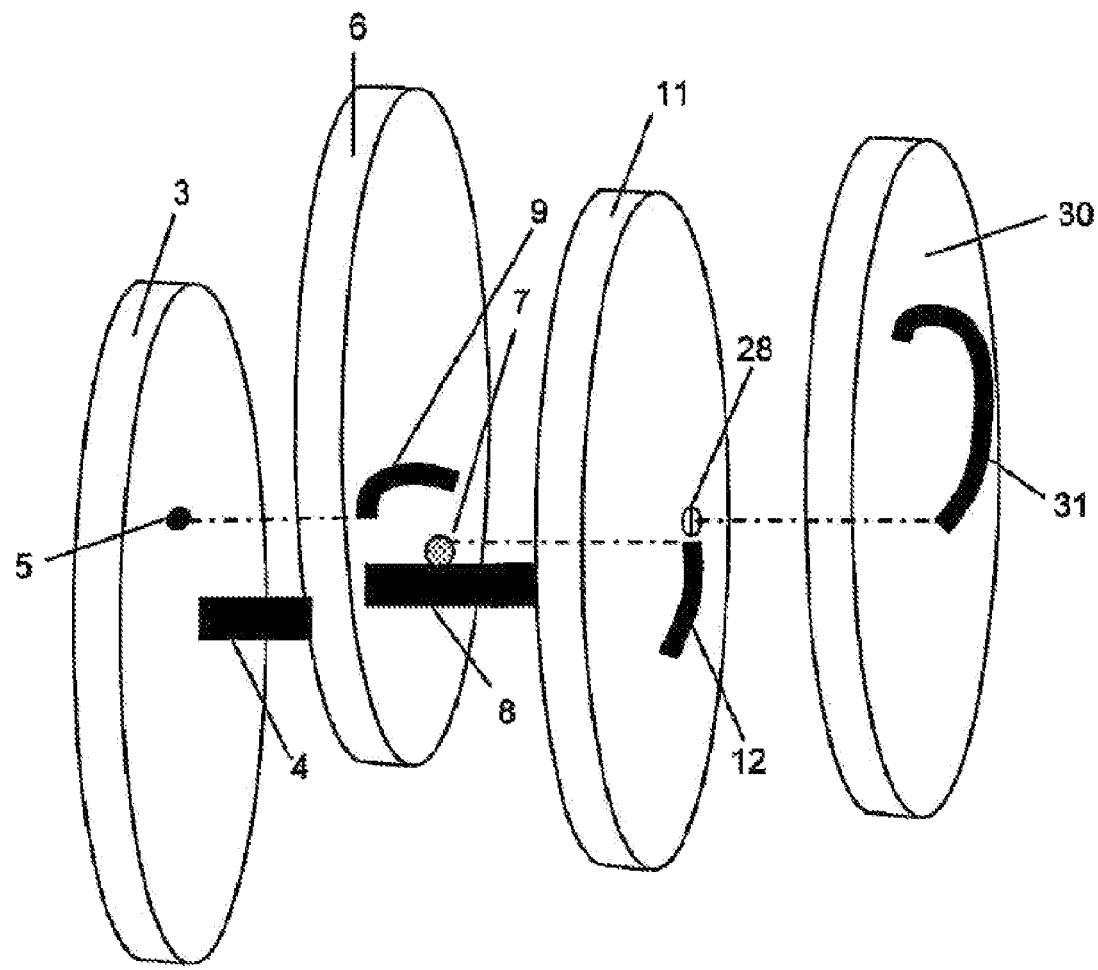

Another embodiment of the motion constraining element is shown in FIG. 9, where the hinge comprises four shells. The inner 3, middle 6, and outer 11 shells are similar to those previously discussed. The fourth shell, a cover shell 30, is situated to the outside of the outer shell 11. In addition, the cover shell is also attached to the proximal arm 2, and thereby to the inner shell 3. There is a cover shell slot 31 for an outer shell protuberance 28 to track. In this configuration, both middle and outer shells can rotate simultaneously relative to each other and the inner shell. However, the rotations of these shells are constrained because the center of the outer shell follows the cover shell slot via tracking of the outer shell protuberance with the cover shell slot. The shape of the cover shell slot is a combination of the outer shell slot (over the first flexion range) and the middle shell slot (over the second flexion range). Thus, for the hinge embodiments shown in FIGS. 4-6, the corresponding cover shell slot is given in FIG. 2(A)-(C), respectively The hinges of the present invention can be used in knee braces. FIG. 10 is one embodiment to correct an abnormally rotated knee comprising a lateral hinge 60 and medial hinge 62. The medial 32, lateral 34 and anterior 36 portions of the thigh cuff comprise the thigh cuff 30. The medial 42, lateral 44, and anterior 46 portions of the tibial cuff comprise the tibial cuff 40. The lateral 60 and medial 62 hinges connect the thigh cuff 30 to the tibial cuff 40. The lateral hinge 60 connects to the lateral portion 34 of the thigh cuff 30 by a proximal lateral arm 50. The lateral hinge 60 connects to the lateral portion 44 of the tibial cuff 40 by a distal lateral arm 54.

The medial hinge 62 connects to the medial portion 32 of the thigh cuff 30 by a proximal medial arm 52. The medial hinge 62 connects to the medial portion 42 of the tibial cuff 40 by a distal medial arm 56. The pad 18, shown in FIG. 3, stabilizes the hinges relative to the knee by transmitting force from the hinges onto the femoral condyle.

The proximal 64 and distal 66 elastic bands are attached to the lateral and medial portions of the thigh 30 and tibial 40 cuffs, respectively. The distal elastic band 66 is preferably located above the muscle belly of the gastrocnemius to prevent the tibial cuff 40 from slipping down the shank during extension and helps stable the distal areas of the knee brace during flexion. The posterior proximal 66 and posterior distal 68 belts connect the proximal arms 50 and 52 and the distal arms 54 and 56, respectively, by wrapping around the leg, posterior to the knee.

In preferred embodiments the tibial cuff 40 can be located slightly distal to the tibial tubercle and stabilized above the muscle belly of the tibialis anterior to avoid slipping down the shank upon extension. The distal 64 and proximal 66 elastic bands are preferably elastic for approximately ten percent strain, and are relatively non-elastic for strains greater than ten percent. The belts 65 and 68 are relatively non-elastic so as to minimize migration of the hinges in an anterior direction during extension. The cuffs 30 and 40 are rigid and can be constructed using fiberglass, or other moldable materials. In addition, the cuffs can be initially molded to provide a basic shape and then heated and formed to a desired shape, thereby maximizing comfort. One example of such a material is reinforced fiber filled thermoplastic resin. The thigh cuff 30 is preferably about two inches wide vertically to prevent anterior rotation during flexion/extension. In addition, elastic bands 64 and 66 help minimize anterior rotation of the thigh cuff 30. The lateral 34 and medial 32 portions of the thigh cuff 30 can be extended proximally to further minimize anterior rotation of 30 in flexion. The distal arms 54 and 56 designs assist in stabilizing the posterolateral and anteromedial corners, respectively, thereby more effectively transmitting rotational forces to the tibia during flexion/extension, thereby restoring the normal envelope of knee motion. For example, 54 can be designed to fasten to the tibial cuff at two locations, thereby increasing stability. Materials suitable for the elastic and non-elastic belts as well as the thigh and tibial cuffs are known to those of ordinary skill in the art. Materials suitable for use in the hinge preferably include materials that provide low friction, including, for example, metal, high-density polyethylene and the like. In addition, friction can be further reduced by coating the surface components to reduce the coefficient of friction.

Means for securing the tibial and thigh cuff to the users tibia and thigh are known in the art, as disclosed in U.S. Pub. Pat. No. 2004/0054311, hereby specifically incorporated by reference. The securing means can include a buckle assembly to snap and then tension the strap, multiple buckle assemblies, velcro, hooks, clamps and other various flexible strap means.

Those of ordinary skill in the art will appreciate that materials and methods other than those specifically described herein can be employed in the practice of this invention without departing from the scope of this invention. For example, the shells can contain more than one shell slot-protuberance tracking, thereby decreasing stress, pressure and friction points between the shells. In addition, any number of additional shells added to the hinge is within the scope of the invention. For clarity, only the right knee and right knee brace were discussed. The principles disclosed in this invention are also applicable for the left knee and left knee brace. The present invention can also correct abnormal rotational alignment (as well as varus and valgus deformity in either knee) where the tibia is abnormally rotated inward, by application of a torque so that the tibia rotates in an external direction.

I claim:
1. A hinge having a variable center of rotation comprising:
   a. an inner shell, a middle shell, and an outer shell, said middle shell rotatably engaged to said inner shell and having an inner-middle shell co-axis and middle shell rotation whereby said middle shell rotates relative to said inner shell, and said outer shell rotatably engaged to said middle shell and having a middle-outer shell co-axis and outer shell rotation whereby said outer shell rotates relative to said middle shell, wherein said inner shell does not rotate, and wherein said inner-middle shell co-axis is located at the center of the inner shell, and said middle-outer shell co-axis is located off-center of said middle shell;
   b. said inner shell further comprising an inner shell protuberance;
   c. said middle shell further comprising a middle shell protuberance, and a middle shell slot through which said inner shell protuberance tracks, wherein said inner shell protuberance tracking constrains said middle shell rotation of said middle shell relative to said inner shell;
   d. said outer shell further comprising an outer shell slot through which said middle shell protuberance tracks, wherein said middle shell protuberance tracking constrains said outer shell rotation of said outer shell relative to said middle shell;
   e. a motion constraining element to prevent rotation of said middle shell relative to said inner shell over a first flexion range as said outer shell rotates relative to said middle shell over said first flexion range and to prevent rotation of said outer shell relative to said middle shell over a second flexion range as said middle shell rotates relative to said inner shell, wherein said second flexion range does not overlap said first flexion range.

2. The hinge of claim 1, wherein the motion constraining element comprises:
   a. the outer shell further comprising an outer shell protuberance;
   b. a cover shell, wherein said cover shell comprises a cover shell slot through which said outer shell protuberance tracks;
   c. wherein said cover shell slot is shaped so that over said first flexion range said cover shell slot has the shape of said outer shell slot and over said second flexion range said cover shell slot has the shape of said middle shell slot.

3. The hinge of claim 1 wherein the middle shell has an outer edge and the motion constraining element comprises:
   a. a bulb operably connected to the outer edge of the middle shell wherein the bulb further comprises
      i. a stem having two ends, the first end rotatably connected to the outer edge of the middle shell;
      ii. four orthogonal arms comprising a first pair of arms and a second pair of arms, wherein the arms are non-rotatably connected to the stem's second end, wherein
         1. the first pair of arms engage with one of the inner and outer shells thereby preventing rotation of the middle shell relative to one of the inner and outer shells, and
         2. the second pair of arms receive a force from one of the inner and outer shells thereby rotating the bulb in a ninety degree increment.

4. The hinge of claim 1 wherein:
   a. said outer shell slot is an arc of approximately 30 degrees of a notional circle having a radius of curvature of between approximately 5 mm to 17 mm, wherein said outer shell slot is positioned anterior to the middle-outer shell co-axis, so that during said first flexion range the center of rotation location varies with flexion, said location constrained by said tracking of said middle shell protuberance with said outer shell slot;
   b. said middle shell slot is an arc of approximately 120 degrees of a notional circle positioned posterior to said inner-middle shell co-axis, when flexion is thirty degrees or less, having a radius of curvature of between approximately 5 mm to 17 mm, so that during said second flexion range the center of rotation location does not vary.

5. The hinge of claim 1 wherein:
   a. said outer shell slot is an arc of approximately 60 degrees of a notional circle positioned anterior to the middle-outer shell co-axis having a radius of curvature of between approximately 5 mm to 17 mm, so that during said first flexion range the center of rotation location varies with flexion, said location constrained by said tracking of said middle shell protuberance with said outer shell slot;
   b. said middle shell slot is an arc of approximately 90 degrees of a notional circle positioned proximal to said inner-middle shell co-axis upon extension, having a radius of curvature of between approximately 5 mm to 17 mm, so that during said second flexion range the center of rotation location varies with flexion.

6. The hinge of claim 1 wherein:
   a. said outer shell slot is an arc of approximately 60 degrees of a notional circle positioned distal to said middle-outer shell co-axis, upon extension, having a radius of curvature of between approximately 5 mm to 17 mm, so that during said first flexion range the center of rotation location varies with flexion, said location constrained by said tracking of said middle shell protuberance with said outer shell slot;
   b. said middle shell slot is an arc of approximately 90 degrees of a notional circle positioned posterior to said inner-middle shell co-axis, upon extension, having a radius of curvature of between approximately 5 mm to 17 mm, so that during said second flexion range the center of rotation location varies with flexion, said location constrained by the tracking of the inner shell protuberance with the middle shell slot.

7. A knee brace comprising one or two of the hinges of claim 1.

8. The knee brace of claim 7 further comprising:
   a. a thigh cuff having a medial portion, a lateral portion and an anterior portion;
   b. a tibial cuff having a medial portion, a lateral portion and an anterior portion;
   c. a proximal lateral arm linked to the lateral portion of said thigh cuff;
   d. a proximal medial arm linked to the medial portion of said thigh cuff;
   e. a distal lateral arm linked to the lateral portion of said tibial cuff;
   f. a distal medial arm linked to the medial portion of said tibial cuff;
   g. a lateral hinge for linking said proximal lateral arm to said distal lateral arm;
   h. a medial hinge for linking said proximal medial arm to said distal medial arm;
   i. a posterior proximal belt linking said proximal lateral arm to said proximal medial arm;
   j. a posterior distal belt linking said distal lateral arm to said distal medial arm;
   k. means to secure said thigh cuff to a wearer's thigh;
   l. means to secure said tibial cuff to a wearer's tibial shank.

9. The knee brace of claim 8 for correcting a varus knee wherein simultaneous motion of the lateral hinge and the medial hinge during flexion generate an unloading force on the medial compartment of the varus knee during extension between about 0 degrees and about 30 degrees of flexion and an internal rotation on the tibia during flexion.

10. The knee brace of claim 8 for correcting a valgus knee, wherein simultaneous motion of the lateral hinge and the medial hinge during flexion generate an unloading force on the lateral compartment of the valgus knee during extension between about 0 degrees and about 30 degrees of flexion and an internal rotation on the tibia during flexion.

11. The knee brace of claim 8 wherein the thigh and tibial cuff securing means comprise a fastenable elastic belt.

12. A method for treating a knee pathology using the hinge of claim 1.

13. The method of claim 12 wherein said knee pathology is an osteoarthritic or osteoarthritic-prone knee.

14. A hinge comprising:
   a. an inner shell, a middle shell, an outer shell, and a cover shell, said middle shell rotatably engaged to said inner shell and having an inner-middle shell co-axis and middle shell rotation, said outer shell rotatably engaged to said middle shell and having a middle-outer shell co-axis and outer shell rotation, wherein said inner shell and cover shell do not rotate, and wherein said inner-middle shell co-axis is located at the center of the inner shell, and said middle-outer shell co-axis is located off-center of said middle shell;
   b. said inner shell further comprising an inner shell protuberance;

c. said middle shell further comprising a middle shell protuberance, and a middle shell slot through which said inner shell protuberance tracks, wherein said inner shell protuberance tracking constrains said middle shell rotation of said middle shell relative to said inner shell;

d. said outer shell further comprising an outer shell protuberance and an outer shell slot through which said middle shell protuberance tracks, wherein said middle shell protuberance tracking constrains said outer shell rotation of said outer shell relative to said middle shell;

e. said cover shell further comprising a cover shell slot through which said outer shell protuberance tracks, wherein said cover shell slot is shaped so that over said first flexion range said cover shell slot has the shape of said outer shell slot and over said second flexion range said cover shell slot has the shape of said middle shell slot;

f. said cover shell and said inner shell connected to a femoral arm.

15. A method for treating a knee pathology comprising:

a. altering an abnormal rotation of the tibia, wherein said altering involves applying a rotational force to the tibia during flexion in a direction opposite to that of said abnormal rotation, and b. applying an off-loading force to the knee, wherein said rotational force and said off-loading force is applied repeatedly during every flexion/extension cycle so as to correct the knee pathology;

wherein said application of rotational force and off-loading force is generated by a combination of a first hinge and a second hinge, the first hinge located medial to the knee and the second hinge located lateral to the knee, wherein said first hinge has a first variable center of rotation and said second hinge has a second variable center of rotation, wherein the first variable center of rotation is defined by tracking of a middle shell protuberance in the medial hinge with an outer shell slot in the medial hinge over a first flexion range, and tracking of an inner shell protuberance in the medial hinge with a middle shell slot in the medial hinge over a second flexion range: and the second variable center of rotation is defined by tracking of a middle shell protuberance in the lateral hinge with an outer shell slot in the lateral hinge over a third flexion range, and tracking of an inner shell protuberance in the lateral hinge with a middle shell slot in the lateral hinge over a fourth flexion range.

16. The method of claim 15 for correcting a varus knee wherein the rotational force is generated by locating the first variable center of rotation of the medial hinge distal to the cylindrical axis generating a distraction force on the femur in extension during the first flexion range, and locating the center of rotation of the lateral hinge proximal to the cylindrical axis during the third flexion range, thereby correcting varus knee malalignment.

17. The method of claim 15 for correcting a valgus knee wherein the rotational force is generated by locating the center of rotation of the lateral hinge distal to the cylindrical axis during the third flexion range, and locating the center of rotation of the medial hinge proximal to the cylindrical axis during the first flexion range, thereby correcting valgus knee malalignment.

18. The method of claim 15 wherein said knee is an osteoarthritic or osteoarthritic-prone knee.

* * * * *